(12) United States Patent
Schultz et al.

(10) Patent No.: US 9,113,950 B2
(45) Date of Patent: Aug. 25, 2015

(54) THERAPEUTIC DELIVERY DEVICE

(75) Inventors: John Richard Schultz, Denver, CO (US); Christopher J. Centeno, Broomfield, CO (US)

(73) Assignee: Regenerative Sciences, LLC, Broomfield, CO (US)

( * ) Notice: Subject to any disclaimer, the term of this patent is extended or adjusted under 35 U.S.C. 154(b) by 494 days.

(21) Appl. No.: 12/939,856

(22) Filed: Nov. 4, 2010

(65) Prior Publication Data

US 2011/0276001 A1     Nov. 10, 2011

Related U.S. Application Data

(60) Provisional application No. 61/258,314, filed on Nov. 5, 2009, provisional application No. 61/258,070, filed on Nov. 4, 2009.

(51) Int. Cl.
| | | |
|---|---|---|
| *A61B 17/34* | (2006.01) | |
| *A61M 25/01* | (2006.01) | |
| *A61M 25/00* | (2006.01) | |

(52) U.S. Cl.
CPC ......... *A61B 17/3415* (2013.01); *A61B 17/3472* (2013.01); *A61M 25/01* (2013.01); *A61M 2025/0096* (2013.01)

(58) Field of Classification Search
CPC ............ A61M 25/01; A61M 25/0102; A61M 2025/0089; A61M 2025/009; A61M 2025/0091; A61M 2025/0096; A61B 17/3472
USPC ............................ 604/164.01, 164.11, 170.03
See application file for complete search history.

(56) References Cited

U.S. PATENT DOCUMENTS

| | | | |
|---|---|---|---|
| 4,832,044 A * | 5/1989 | Garg .............................. | 600/566 |
| 5,198,357 A | 3/1993 | Holmovist et al. | |
| 5,221,253 A | 6/1993 | Coll | |
| 5,226,914 A | 7/1993 | Caplan et al. | |
| 5,292,330 A | 3/1994 | Shutt | |
| 5,486,359 A | 1/1996 | Caplan et al. | |
| 5,693,341 A * | 12/1997 | Schroeder et al. ............ | 424/488 |
| 5,736,396 A | 4/1998 | Bruder et al. | |
| 5,749,874 A | 5/1998 | Schwartz | |
| 5,769,899 A | 6/1998 | Schwartz et al. | |
| 5,788,713 A * | 8/1998 | Dubach et al. ................ | 606/130 |

(Continued)

FOREIGN PATENT DOCUMENTS

| | | |
|---|---|---|
| KR | 2003 024028 | 3/2003 |
| WO | WO 97/34614 | 9/1997 |

(Continued)

OTHER PUBLICATIONS

Acosta et al (2005) "The Potential Role of Mesenchymal Stem Cell Therapy for Intervertebral Disc Degeneration: A Critical Overview" Neurosurg. Focus 19(3):E4.

(Continued)

*Primary Examiner* — Laura Bouchelle
(74) *Attorney, Agent, or Firm* — Swanson & Bratschun, L.L.C.

(57) ABSTRACT

Methods and device are provided for delivery of biologics to an intervertebral disc. Device described herein include a needle assembly and handle assembly that optimize biologic delivery parameters to a target location within a disc. The needle assembly includes the capability of advancing into the disc at pre-configured pathways that allow for minimized damaged and maximized positioning of the biologic.

34 Claims, 17 Drawing Sheets

(56) References Cited

U.S. PATENT DOCUMENTS

| | | | |
|---|---|---|---|
| 5,842,477 | A | 12/1998 | Naughton et al. |
| 5,980,504 | A | 11/1999 | Sharkey et al. |
| 6,007,570 | A | 12/1999 | Sharkey et al. |
| 6,073,051 | A | 6/2000 | Sharkey et al. |
| 6,095,149 | A | 8/2000 | Sharkey et al. |
| 6,099,514 | A | 8/2000 | Sharkey et al. |
| 6,122,549 | A | 9/2000 | Sharkey et al. |
| 6,126,682 | A | 10/2000 | Sharkey et al. |
| 6,200,606 | B1 | 3/2001 | Peterson et al. |
| 6,217,527 | B1* | 4/2001 | Selmon et al. ............ 600/585 |
| 6,245,054 | B1 | 6/2001 | Fuimaono et al. |
| 6,258,086 | B1 | 7/2001 | Ashley et al. |
| 6,261,311 | B1 | 7/2001 | Sharkey et al. |
| 6,283,960 | B1 | 9/2001 | Ashley |
| 6,409,727 | B1 | 6/2002 | Bales et al. |
| 6,517,568 | B1 | 2/2003 | Sharkey et al. |
| 6,530,956 | B1 | 3/2003 | Mansmann |
| 6,547,810 | B1 | 4/2003 | Sharkey et al. |
| 6,562,033 | B2 | 5/2003 | Shah et al. |
| 6,595,959 | B1 | 7/2003 | Stratienko |
| 6,604,003 | B2 | 8/2003 | Fredricks et al. |
| 6,623,733 | B1 | 9/2003 | Hossainy et al. |
| 6,638,276 | B2 | 10/2003 | Sharkey et al. |
| 6,699,471 | B2 | 3/2004 | Marco et al. |
| 6,699,484 | B2 | 3/2004 | Whitmore et al. |
| 6,726,685 | B2 | 4/2004 | To et al. |
| 6,733,496 | B2 | 5/2004 | Ashley et al. |
| 6,821,276 | B2 | 11/2004 | Lambrecht et al. |
| 6,832,997 | B2 | 12/2004 | Uchida et al. |
| 6,835,377 | B2 | 12/2004 | Goldberg et al. |
| 6,872,567 | B2 | 3/2005 | Thomas et al. |
| 7,069,087 | B2 | 6/2006 | Sharkey et al. |
| 7,229,959 | B1 | 6/2007 | Drohan et al. |
| 7,322,962 | B2 | 1/2008 | Forrest |
| 7,896,909 | B2 | 3/2011 | Sharkey et al. |
| 7,905,863 | B1* | 3/2011 | Forrest ............... 604/164.01 |
| 2001/0031963 | A1 | 10/2001 | Sharkey et al. |
| 2002/0022830 | A1 | 2/2002 | Sharkey et al. |
| 2002/0110544 | A1 | 8/2002 | Goldberg et al. |
| 2003/0050709 | A1 | 3/2003 | North et al. |
| 2003/0181964 | A1 | 9/2003 | Sharkey et al. |
| 2003/0224411 | A1 | 12/2003 | Stanton et al. |
| 2003/0225331 | A1 | 12/2003 | Diederich et al. |
| 2004/0015215 | A1 | 1/2004 | Fredrick et al. |
| 2004/0015218 | A1 | 1/2004 | Finch et al. |
| 2004/0078077 | A1 | 4/2004 | Binette et al. |
| 2004/0083002 | A1 | 4/2004 | Belef et al. |
| 2004/0087994 | A1 | 5/2004 | Suddaby |
| 2004/0102824 | A1 | 5/2004 | Sharkey et al. |
| 2004/0111136 | A1 | 6/2004 | Sharkey et al. |
| 2004/0111137 | A1 | 6/2004 | Shankey et al. |
| 2004/0127963 | A1 | 7/2004 | Uchida et al. |
| 2004/0136968 | A1 | 7/2004 | Zheng et al. |
| 2004/0193045 | A1 | 9/2004 | Scarborough et al. |
| 2004/0229786 | A1 | 11/2004 | Attawia et al. |
| 2004/0235166 | A1 | 11/2004 | Prockop et al. |
| 2005/0019865 | A1 | 1/2005 | Kihm et al. |
| 2005/0038520 | A1 | 2/2005 | Binette et al. |
| 2005/0100536 | A1 | 5/2005 | Mishra |
| 2005/0118230 | A1 | 6/2005 | Hill et al. |
| 2005/0276792 | A1 | 12/2005 | Kaminski et al. |
| 2006/0073124 | A1 | 4/2006 | Garcia Castro et al. |
| 2007/0122904 | A1 | 5/2007 | Nordon |
| 2007/0128722 | A1 | 6/2007 | Lin et al. |
| 2008/0038233 | A1 | 2/2008 | Freemont et al. |
| 2008/0051756 | A1* | 2/2008 | Makower et al. .......... 604/508 |
| 2009/0010896 | A1 | 1/2009 | Centeno et al. |
| 2009/0177161 | A1* | 7/2009 | McGuckin et al. ...... 604/164.11 |
| 2009/0208464 | A1 | 8/2009 | Centeno |
| 2010/0168022 | A1 | 7/2010 | Centeno |
| 2011/0052533 | A1 | 3/2011 | Centeno |
| 2011/0054929 | A1 | 3/2011 | Centeno |
| 2011/0200642 | A1 | 8/2011 | Centeno |
| 2011/0245804 | A1 | 10/2011 | Centeno |

FOREIGN PATENT DOCUMENTS

| | | |
|---|---|---|
| WO | WO 98/51317 | 11/1998 |
| WO | WO 01/80865 | 11/2001 |
| WO | WO 2004/067704 | 8/2004 |
| WO | WO 2005/046761 | 5/2005 |
| WO | WO 2007/087519 | 8/2007 |
| WO | WO 2008/034803 | 3/2008 |
| WO | WO 2009/006161 | 1/2009 |
| WO | WO 2009/085969 | 7/2009 |
| WO | WO 2009/114785 | 9/2009 |
| WO | WO 2010/065854 | 6/2010 |

OTHER PUBLICATIONS

Ahuja et al (1995) "Identification of Two Subpopulations of Rat Monocytes Expressing Disparate Molecular Forms and Quantities of CD43" Cell Immunol. 163(1):59-69.

Alhadlaq and Mao (2004) "Mesenchymal Stem Cells: Isolation and Therapeutics" Stem Cells Dev. 13(4):436-448.

Anitua et al (2004) "Autologous Platelets as a Source of Proteins for Healing and Tissue Regeneration" Thromb. Haemost. 91:4-15.

Baecher-Allan et al (2005) "Functional Analysis of Highly Defined, FACS-Isolated Populations of Human Regulatory CD4+CD25+ T Cells" Clinical Immunology 115:10-18.

Barry (2003) "Mesenchymal Stem Cell Therapy in Joint Disease" Novartis Found. Symp. 249:86-102, 170-4, 239-41.

Bensaïd et al (2003) "A Biodegradable Fibrin Scaffold for Mesenchymal Stem Cell Transplantation" Biomaterials 24:2497-2502.

Bernardo et al (2007) "Optimization of In Vitro Expansion of Human Multipotent Mesenchymal Stromal Cells for Cell-Therapy Approaches: Further Insights in the Search for a Fetal Calf Serum Substitute" J. Cell. Physiol. 211:121-130.

Billard et al (2000) "Switch in the Protein Tyrosine Phosphatase Associated with Human CD100 Semaphorin at Terminal B-Cell Differentiation Stage" Blood 95(3):965-972.

Bircher et al (1988) "Discitis Following Lumbar Surgery" Spine 13(1):98-102.

Borner and Follath (1989) "Antibiotic Therapy and Long-Term Outcome in Patients with Vertebral Osteomyelitis" Schweiz Med. Wochenschr. 119(1):19-21 (German, English Abstract Only).

Brisby et al (2004) "Cell Therapy for Disc Degeneration-Potentials and Pitfalls" Orthop. Clin. North Am. 35(1):85-93.

Buckwalter and Mankin (1998) "Articular Cartilage: Degeneration and Osteoarthritis, Repair, Regeneration, and Transplantation" AAOS Instr. Course Lect. 47:487-504.

Bühring et al (1999) "The Monoclonal Antibody 97A6 Defines a Novel Surface Antigen Expressed on Human Basophils and Their Multipotent and Unipotent Progenitors" Blood 94(7):2343-2356.

Caligiuri et al (1990) "Functional Consequences of Interleukin 2 Receptor Expression on Resting Human Lymphocytes. Identification of a Novel Natural Killer Cell Subset with High Affinity Receptors" J. Exp. Med. 171:1509-1526.

Caplan and Bruder (2001) "Mesenchymal Stem Cells: Building Blocks for Molecular Medicine in the 21st Century" Trends Mol. Med. 7(6):259-264.

Caplan (1991) "Mesenchymal Stem Cells" J. Orthop. Res. 9(5):641-650.

Cashman et al (1990) "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-Beta" Blood 75(1):96-101.

Cassiede et al (1996) "Osteochondrogenic Potential of Marrow Mesenchymal Progenitor Cells Exposed to TGF-β1 or PDGF-BB as Assayed In Vivo and In Vitro" J. of Bone and Miner. Res. 11(9):1264-1273.

Centeno et al (2006) "Partial Regeneration of the Human Hip Nucleated Cell Transfer: A Case Study" Pain Physician 9:253-256.

Charalambous et al (2003) "Septic Arthritis Following Intra-Articular Steroid Injection of the Knee—a Survey of Current Practice Regarding Antiseptic Technique used During Intra-Articular Steroid Injection of the Knee" Clin. Rheumatol. 22:386-390.

(56) References Cited

OTHER PUBLICATIONS

Chazerain et al (1999) "Septic Hip Arthritis After Multiple Injections into the Joint of Hyaluronate and Glucocorticoid" Rev. Rhum. Engl. Ed. 66(7-9):436-437.
Crisostomo et al (2006) "High Passage Number of Stem Cells Adversely Affects Stem Cell Activation and Myocardial Protection" Shock 26(6):575-580.
D'Ippolito et al (1999) "Age-Related Osteogenic Potential of Mesenchymal Stromal Stem Cells from Human Verterbral Bone Marrow" J. Bone Miner. Res. 14(7):1115-122.
Dall et al (1987) "Postoperative Discitis. Diagnosis and Management" Clin. Orthop. Relat. Res. 224:138-146.
Del Curling et al (1990) "Changing Concepts in Spinal Epidural Abscess: A Report of 29 Cases" Neurosurgery 27(2):185-192.
Deschaseaux et al (2003) "Direct Selection of Human Bone Marrow Mesenchymal Stem Cells Using an Anti-CD49a Antibody Reveals Their $CD45^{med,low}$ Phenotype" British Journal of Haematology 122:506-517.
Doucet et al (2005) "Platelet Lysates Promote Mesenchymal Stem Cell Expansion: A Safety Substitute for Animal Serum in Cell-Based Therapy Applications" J. Cell. Physiol. 205:228-236.
Elghetany and Patel (2002) "Assessment of CD24 Expression on Bone Marrow Neutrophilic Granulocytes: CD24 is a Marker for the Myelocytic Stage of Development" Am. J. Hematol. 71:348-349.
Fang et al (2004) "Biocompatibility Studies on Fibrin Glue Cultured with Bone Marrow Mesenchymal Stem Cells In Vitro" J. of Huazhong. Univ. of Sci. Technolog. Med. Sci. 24(3):272-274.
Fiedler et al (2002) "BMP-2, BMP-4, and PDGF-bb Stimulate Chemotactic Migration of Primary Human Mesenchymal Progenitor Cells" J. Cell. Biochem. 87:305-312.
Fiedler et al (2004) "To Go or Not to Go: Migration of Human Mesenchymal Progenitor Cells Stimulated by Isoforms of PDGF" J. Cell. Biochem. 93:990-998.
Fortier et al (1998) "Isolation and Chondrocytic Differentiation of Equine Bone Marrow-Derived Mesenchymal Stem Cells" Am. J. Vet. Res. 59(9):1182-1187.
Fraser et al (1993) "Each Hypersensitive Site of the Human Beta-Globin Locus Control Region Confers a Different Developmental Pattern of Expression on the Globin Genes" Genes & Development 7:106-113.
Fujiwara et al (1994) "Acute Purulent Discitis with Epidural Abscess of the Cervical Spine in an Adult" Neurol. Med. Chir. (Tokyo) 34(6):382-384.
Gazzit et al (1995) "Purified $CD34^+$ $Lin^-$ $Thy^+$ Stem Cells do Not Contain Clonal Myeloma Cells" Blood 86(1):381-389.
Gibson and Waddell (2005) "Surgery for Degenerative Lumbar Spondylosis: Updated Cochrane Review" Spine 30(20):2312-2320.
Gruber and Hanley (2003) "Recent Advances in Disc Cell Biology" Spine 28(2):186-193.
Gruber et al (2004) "Platelet-Released Supernatants Increase Migration and Proliferation, and Decrease Osteogenic Differentiation of Bone Marrow-Derived Mesenchymal Progenitor Cells Under In Vitro Conditions" Platelets 15(1):29-35.
Gustafson et al (1989) "Further Investigations into the Potentiation of Infection by Intra-Articular Injection of Polysulfated Glycosaminoglycan and the Effect of Filtration and Intra-Articular Injection of Amikacin" Am. J. Vet. Res. 50(12):2018-2022.
Hickstein et al (1992) "Identification of the Promoter of the Myelomonocytic Leukocyte Integrin CD11b" Proc. Natl. Acad. Sci. USA 89(6):2105-2109.
Hirschi et al (1999) "Endothelial Cells Modulate the Proliferation of Mural Cell Precursors Via Platelet-Derived Growth Factor-BB and Heterotypic Cell Contact" Circ. Res. 84(3):298-305.
Hoelscher et al (2000) "Effects of Very High Antibiotic Concentrations on Human Intervertebral Disc Cell Proliferation, Viability, and Metabolism In Vitro" Spine 25(15):1871-1877.
Huang and Terstappen (1994) "Formation of Haematopoietic Microenvironment and Haematopoietic Stem Cells from Single Human Bone Marrow Stem Cells" Nature 368(6472):664.
Huss (2000) "Perspectives on the Morphology and Biology of CD34-Negative Stem Cells" J. Hematother. Stem Cell Res. 9:783-793.
Iversen et al (1992) "Prognosis in Postoperative Discitis, A Retrospective Study of 111 Cases" Acta Orthop. Scand. 63(3):305-309.
Johnstone and Yoo (1999) "Autologous Mesenchymal Progenitor Cells in Articular Cartilage Repair" Clin. Orthop. Relat. Res. 367 Suppl:S156-162.
Kambin and Schaffer (1989) "Percutaneous Lumbar Discectomy Review of 100 Patients and Current Practice" Clin. Orthop. Relat. Res. 238:24-34.
Kang et al (2005) "Role of c-Jun N-Terminal Kinase in the PDGF-Induced Proliferation and Migration of Human Adipose Tissue-Derived Mesenchymal Stem Cells" J. Cell. Biochem. 95:1135-1145.
Kaps et al (2002) "Human Platelet Supernatant Promotes Proliferation but Not Differentiation of Articular Chondrocytes" Med. Biol. Eng. Comput. 40(4):485-490.
Katz et al (1987) "Effect of Platelet-Derived Growth Factor on Enriched Populations of Haemopoietic Progenitors from Patients with Chronic Myeloid Leukaemia" Leuk. Res. 11(4):339-344.
Kilian et al (2004) "Effects of Platelet Growth Factors on Human Mesenchymal Stem Cells and Human Endothelial Cells in Vitro" Eur. J. Med. Res. 9(7):337-344.
Kirshenbaum et al (1999) "Demonstration that Human Mast Cells Arise from a Progenitor Cell Population that is CD34+, c-kit+, and Expresses Aminopeptidase N (CD13)" Blood 94:2333-2342.
Kitoh et al (2004) "Transplantation of Marrow-Derived Mesenchymal Stem Cells and Platelet-Rich Plasma During Distraction Osteogenesis—a Preliminary Result of Three Cases" Bone 35:892-898.
Koh et al (2005) "Co-Culture of Human CD34+ Cells with Mesenchymal Stem Cells Increases the Survival of CD34+ Cells Against the 5-Aza-Deoxycytidine- or Trichostatin A-Induced Cell Death" Biochem. Biophys. Res. Commun. 329:1039-1045.
Kortelainen and Sarkioja (1990) "Fatal Complications of Intramuscular and Intra-Articular Injections" Z Rechtsmed. 103:547-554.
Laiho and Kotilainen (2001) "Septic Arthritis Due to Prevotella Bivia After Intra-Articular Hip Joint Injection" Joint Bone Spine 68:443-444.
Luyten (2004) "Mesenchymal Stem Cells in Osteoarthritis" Curr. Opin. Rheumatol. 16:599-603.
Magne et al (2005) "Mesenchymal Stem Cell Therapy to Rebuild Cartilage" Trends Mol. Med. 11(11):519-526.
Martineau et al (2004) "Effects of Calcium and Thrombin on Growth Factor Release from Platelet Concentrates: Kinetics and Regulation of Endothelial Cell Proliferation" Biomaterials 25:4489-4502.
Medina et al (2000) "Purification of Human Tonsil Plasma Cells: Pre-Enrichment Step by Immunomagnetic Selection of $CD31^+$ Cells" Cytometry 39(3):231-234.
Miyata et al (2005) "Platelet-Derived Growth Factor-BB (PDGF-BB) Induces Differentiation of Bone Marrow Endothelial Progenitor Cell-Derived Cell Line TR-BME2 into Mural Cells, and Changes the Phenotype" J. Cell. Physiol. 204:948-955.
Morshed et al (2004) "Septic Arthritis of the Hip and Intrapelvic Abscess Following Intra-Articular Injection of Hylan G-F 20. A Case Report" J. Bone Joint Surg. Am. 86:823-826.
Munirah et al (2008) "Autologous Versus Pooled Human Serum for Articular Chondrocyte Growth" Journal of Orthopedic Surgery 16(2):220-229.
Müller et al (2006) "Animal Serum-Free Culture Conditions for Isolation and Expansion of Multipotent Mesenchymal Stromal Cells from Human BM" Cytotherapy 8(5):437-444.
Murphy et al (2003) "Stem Cell Therapy in a Caprine Model of Osteoarthritis" Arthritis Rheum. 48(12):3464-3474.
Murray et al (1999) "CD109 is Expressed on a Subpopulation of $CD34^+$ Cells Enriched in Hematopoietic Stem and Progenitor Cells" Exp. Hematol. 27:1282-1294.
Nakayama et al (2000) "Evaluation of Glycosaminoglycans Levels in Normal Joint Fluid of the Knee" J. Nippon Med. Sch. 67(2)92-95.
Nielsen et al (1990) "Postoperative Discitis. Radiology of Progress and Healing" Acta Radiol. 31(6):559-563.
Office Action Final mailed Sep. 22, 2010 with respect to U.S. Appl. No. 11/773,774.

(56) References Cited

OTHER PUBLICATIONS

Office Action mailed Nov. 6, 2009 with respect to U.S. Appl. No. 11/773,774.
Olweus et al (1995) "CD64/Fc Gamma RI is a Granulo-Monocytic Lineage Marker on CD34+ Hematopoietic Progenitor Cells" Blood 85(9):2402-2413.
Onofrio (1980) "Intervertebral Discitis: Incidence, Diagnosis, and Management" Clin. Neurosurg. 27:481-516.
Ordog et al (2004) "Purification of Interstitial Cells of Cajal by Fluorescence-Activated Cell Sorting" Am. J. Physiol. Cell Physiol 286(2):448-456.
Orpen and Birch (2003) "Delayed Presentation of Septic Arthritis of a Lumbar Facet Joint after Diagnostic Facet Joint Injection" J. Spinal Disord. Tech. 16(3):285-287.
Oshima et al (2004) "Fate of Transplanted Bone-Marrow-Derived Mesenchymal Cells During Osteochondral Repair using Transgenic Rats to Simulate Autologous Transplantation" OsteoArthritis Cartilage 12:811-817.
Otawa et al (2000) "Comparative Multi-Color Flow Cytometric Analysis of Cell Surface Antigens in Bone Marrow Hematopoietic Progenitors Between Refractory Anemia and Aplastic Anemia" Leukemia Research 24:359-366.
Park et al (2005) "Thoughts and Progress, Tissue-Engineered Cartilage Using Fibrin/Hyaluronan Composite Gel and its In Vivo Implantation" Artif. Organs 29(10):838-860.
Pellaton et al (1981) "Spectic Arthritis Following Repeated Intraarticular Injections of Glycosaminoglycanpolysulfat (Arteparon®) and Steroids for Osteoarthrosis of the Knee Joint" (French, English Abstract Only) Schweiz. Rudnsch. Med. Prax. 70(52):2364-2367.
Pietramaggiori et al (2006) "Freeze-Derived Platelet-Rich Plasma Shows Beneficial Healing Properties in Chronic Wounds" Wound Rep. Reg. 14:573-580.
Ponte and McDonald (1992) "Septic Discitis Resulting from *Escherichia coli* Urosepsis" J. Fam. Pract. 34(6):767-771.
Rasmusson et al (2003) "Mesenchymal Stem Cells Inhibit the Formation of Cytotoxic T Lymphocytes, but Not Activated Cytotoxic T Lymphocytes or Natural Killer Cells" Transplantation 76(8):1208-1213.
Reddi and Cunningham (1990) "Bone Induction by Osteogenin and Bone Morphogenetic Proteins" Biomaterials 11:33-34.
Richardson et al (2006) "Intervertebral Disc Cell-Mediated Mesenchymal Stem Cell Differentiation" Stem Cells 24:707-716.
Roberts et al (2003) "Autologous Chondrocyte Implantation for Cartilage Repair: Monitoring its Success by Magnetic Resonance Imaging and Histology" Arthritis Research and Therapy 5(1):R60-R73.
Rolf et al (1999) "Intra-Articular Absorption and Distribution of Ketoprofen After Topical Plaster Application and Oral Intake in 100 Patients Undergoing Knee Arthroscopy" Rheumatology 38:564-567.
Ruszymah (2004) "Autologous Human Fibrin as the Biomaterial for Tissue Engineering" Med. J. Malaysia 59 Suppl.B:30-1.
Sah et al "Effects of Fibrin Glue Components on Chondrocyte Growth and Matrix Formation," in 49th Annual Meeting of the Orthopaedic Research Society, poster #0721.
Sanchez et al (2003) "Is Platelet-Rich Plasma the Perfect Enhancement Factor? A Current Review" Int. J. Oral Maxillofac. Implants 18:93-103.
Sato et al (1999) "Reversible Expression of CD34 by Murine Hematopoietic Stem Cells" Blood 94(8):2548-2554.
Silverman et al (Jun. 1999) "Injectable Tissue-Engineered Cartilage Using a Fibrin Glue Polymer" Plast. Reconstr. Surg. 103(7):1809-1818.
Simmons and Torok-Storb (1991) "CD34 Expression by Stromal Precursors in Normal Human Adult Bone Marrow" Blood 78(11):2848-2853.
Singer et al (1987) "Simian Virus 40-Transformed Adherent Cells From Human Long-Term Marrow Cultures: Cloned Cell Lines Produce Cells with Stromal and Hematopoietic Characteristics" Blood 70(2):464-474.
Singer et al (1984) "Evidence for a Stem Cell Common to Hematopoiesis and its In Vitro Microenvironment: Studies of Patients with Clonal Hematopoietic Neoplasia" Leuk. Res. 8(4):535-545.
Spaggiari et al (2006) "Mesenchymal Stem Cell-Natural Killer Cell Interactions: Evidence that Activated NK Cells are Capable of Killing MSCs, Whereas MSCs can Inhibit IL-2-Induced NK-Cell Proliferation" Blood 107(4):1484-1490.
Stacey et al (2000) "Randomised Double-Blind Placebo Controlled Trial of Topical Autologous Platelet Lysate in Venous Ulcer Healing" Eur. J. Vasc. Endovasc. Surg. 20:296-301.
Terstappen et al (1991) "Sequential Generations of Hematopoietic Colonies Derived From Single Nonlineage-Committed CD34+CD38-Progenitor Cells" Blood 77(6):1218-1227.
Toba et al (1999) "Novel Technique for the Direct Flow Cytofluorometric Analysis of Human Basophils in Unseparated Blood and Bone Marrow, and the Characterization of Phenotype and Peroxidase of Human Basophils" Cytometry 35(3):249-259.
Tondreau et al (2004) "Isolation of BM Mesenchymal Stem Cells by Plastic Adhesion or Negative Selection: Phenotype, Proliferation Kinetics and Differentiation Potential" Cyrotherapy 6(4):372-379.
Ueda et al (2007) "Induction of Senile Osteoporosis in Normal Mice by Intra-Bone Marrow-Bone Marrow Transplantation from Osteoporosis-Prone Mice" Stem Cells 25(6):1356-1363.
Weber (1988) "Infectious Damage to the Intervertebral Disk-Before and Following Discotomy" Z. Orthop Ihre Grenzeb 126(5):555-562 (German, English Abstract Only).
Willems et al (Jun. 2004) "Lumbar Discography: Should we Use Prophylactic Antibiotics? A Study of 435 Consecutive Discograms and a Systematic Review of the Literature" J. Spinal Disord. Tech. 17(3):243-247.
Willheim et al (1995) "Purification of Human Basophils and Mast Cells by Multistep Separation Technique and mAb to CDw17 and CD117/c-kit" J. Immunological Methods 182:115-129.
Xaymardan et al (2004) "Platelet-Derived Growth Factor-AB Promotes the Generation of Adult Bone Marrow-Derived Cardiac Myocytes" Circ Res. 94(5):E39-E45.
Yamada et al (2003) "Bone Regeneration Following Injection of Mesenchymal Stem Cells and Fibrin Glue with a Biodegradable Scaffold" J. Cranio-Maxillofac. Surg. 31:27-33.
Zhu et al (2006) "Hypoxia and Serum Deprivation-Induced Apoptosis in Mesenchymal Stem Cells" Stem Cells 24:416-425.
Gajdusek et al (1993) "Basic Fibroblast Growth Factor and Transforming Growth Factor Beta-1: Synergistic Mediators of Angiogenesis In Vitro" J. Cell. Physiol. 157(1):133-144.
Luis A. Solchaga et al (2002) "Treatment of Osteochondral Defects with Autologous Bone Marrow in a Hyaluronan-Based Delivery Vehicle", Tissue Engineering, vol. 8, No. 2, pp. 333-347.
Prins et al (1982) "Effect of Purified Growth Factors on Rabbit Articular Chondrocytes in Monolayer Culture. II. Sulfated Proteoglycan Synthesis" Arthritis & Rheumatism, 25(10):1228-1238.
Yang et al (1994) "Cardioprotective Effects of Platelets Against Ischaemia-Reperfusion Injury are Related in Part to Platelet Glutathione Redox Cycle" Cardiovasc. Res. 28(10):1586-1593 Abstract.
Ye et al (2007) "Effect of Three Growth Factors on Proliferation and Cell Phenotype of Human Fetal Meniscal Cells" Chinese Journal Reconstructive Surgery 21(10):1137-1138 with English Abstract.
Zhu et al (2001) "Recombinant Human Acidic Fibroblast Growth Factor Accelerates the Healing of Full-Thickness Dermal Wounds in Pigs" Modern Rehabilitation 5(9):31 with English Abstract.
Lange et al (2007) "Accelerated and Safe Expansion of Human Mesenchymal Stromal Cells in Animal Serum-Free Medium for Transplantation and Regenerative Medicine" Journal of Cellular Physiology 213(1):18-26.
Schallmoser et al (2007) "Human Platelet Lysate Can Replace Fetal Bovine Serum for Clinical-Scale Expansion of Functional Mesenchymal Stromal Cells" Transfusion 47(8):1436-1446.
Ando et al (2007) "Cartilage repair using an in vitro generated scaffold-free tissue-engineered construct derived from porcine synovial mesenchymal stem cells" Biomaterials 1-9. Available Website: www.sciencedirect.com.

(56) References Cited

OTHER PUBLICATIONS

Castro et al (2002) "Failure of Bone Marrow Cells to Transdifferentiate into Neutral Cells In Vivo" Science 297:1299.

Centeno et al (2008) "Regeneration of meniscus cartilage in a knee treated with percutaneously implanted autologous mesenchymal stem cells" Medical Hypotheses 71:900-908.

Centeno and Faulkner (2012) "The Use of Mesenchymal Stem Cells in Orthopedics" Stem Cells and Cancer Stem Cells 1:173-179.

Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Adherent Technique).

Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Novel Technique).

Mezey et al and Castro et al (2003) "Comment on and Response to Comment on Failure of Bone Marrow Cells to Transdifferentiate into Neutral Cells In Vivo" Science 299:1184b-1184c.

Tosh et al (2002) "Conversion of Pancreatic Cells to Hepatocytes" Biochem. Soc. Trans. 30:51-55.

* cited by examiner

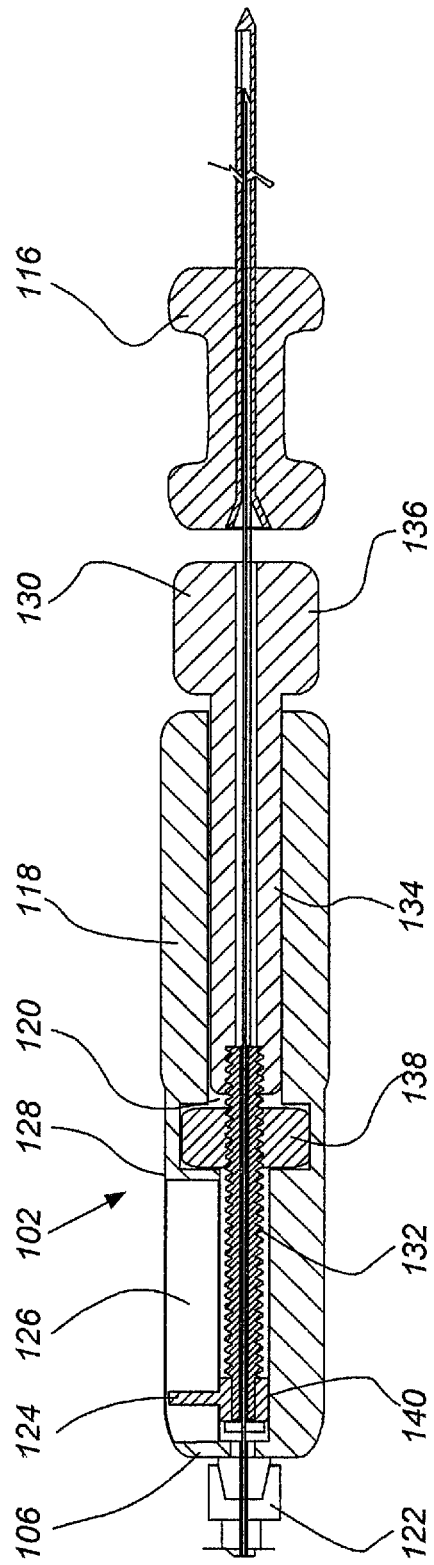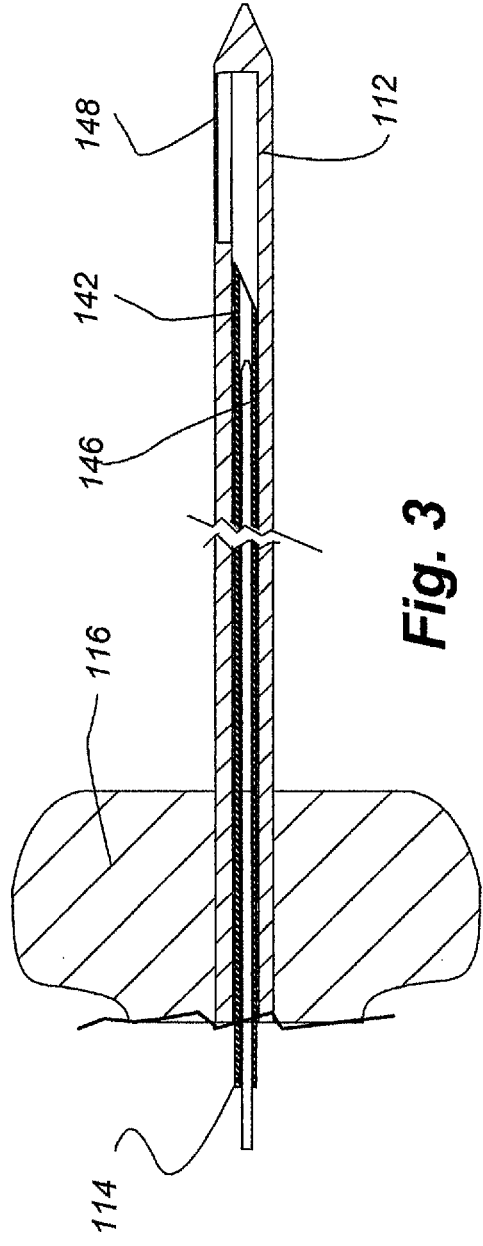
Fig. 2
Fig. 3

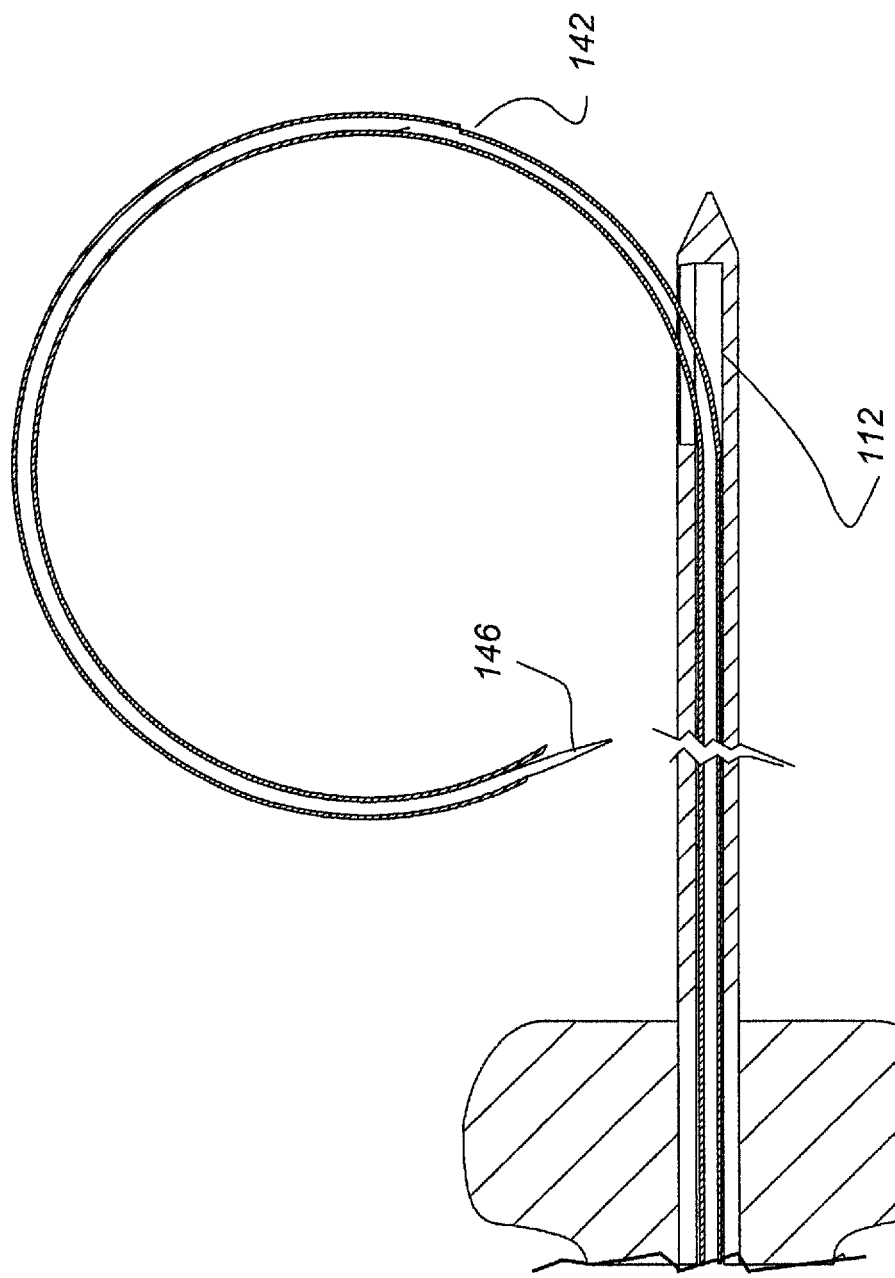

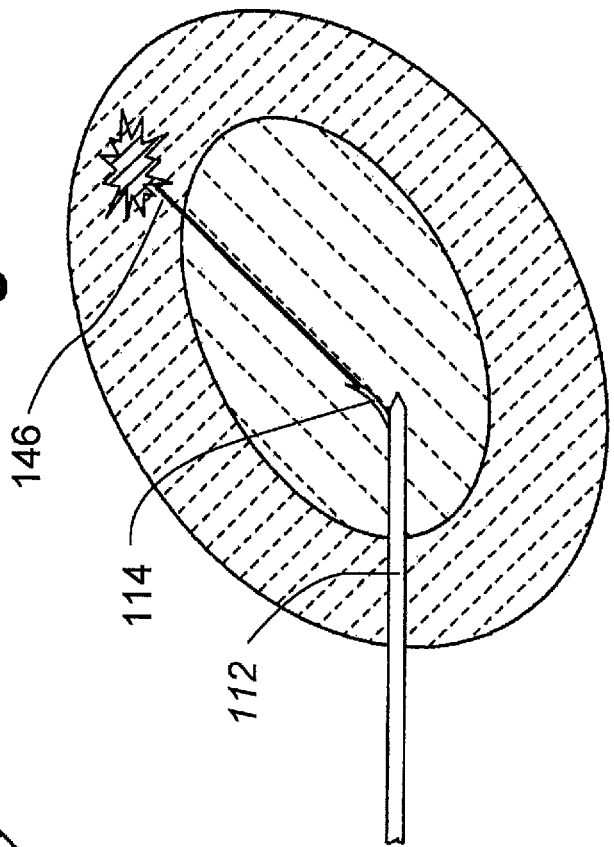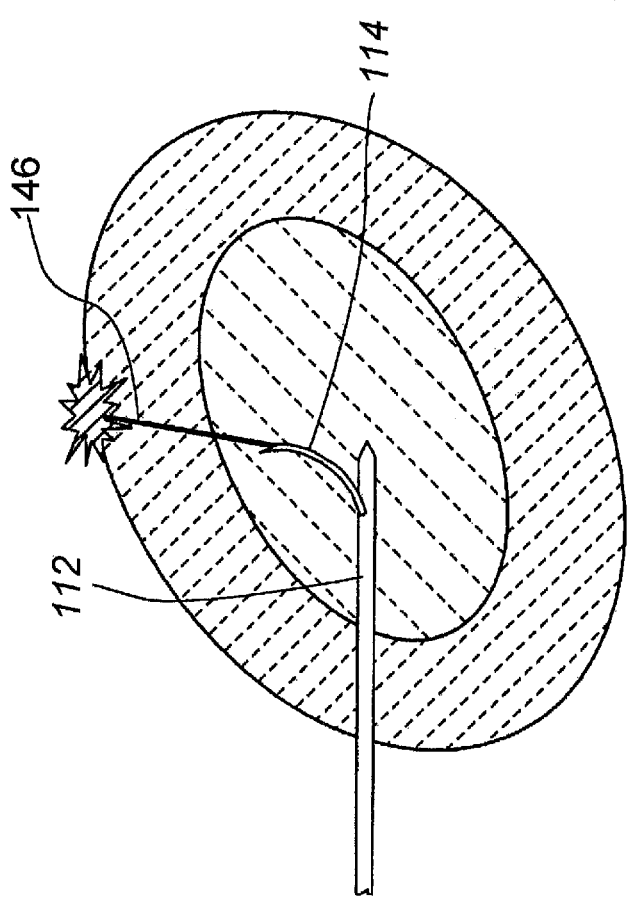

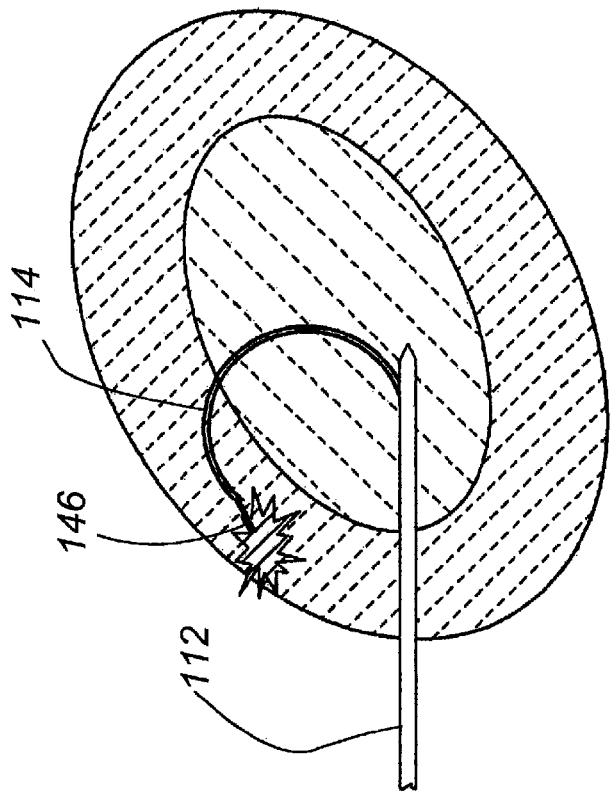
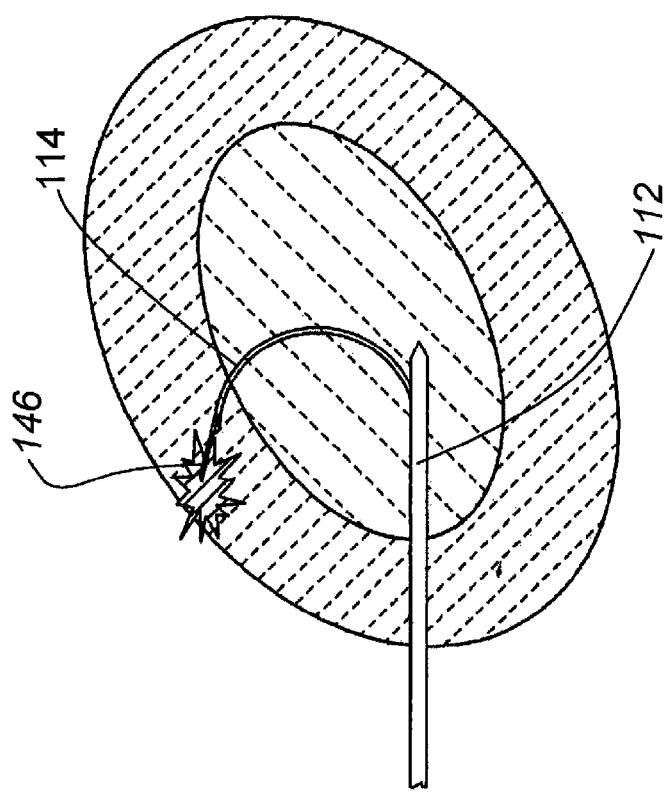

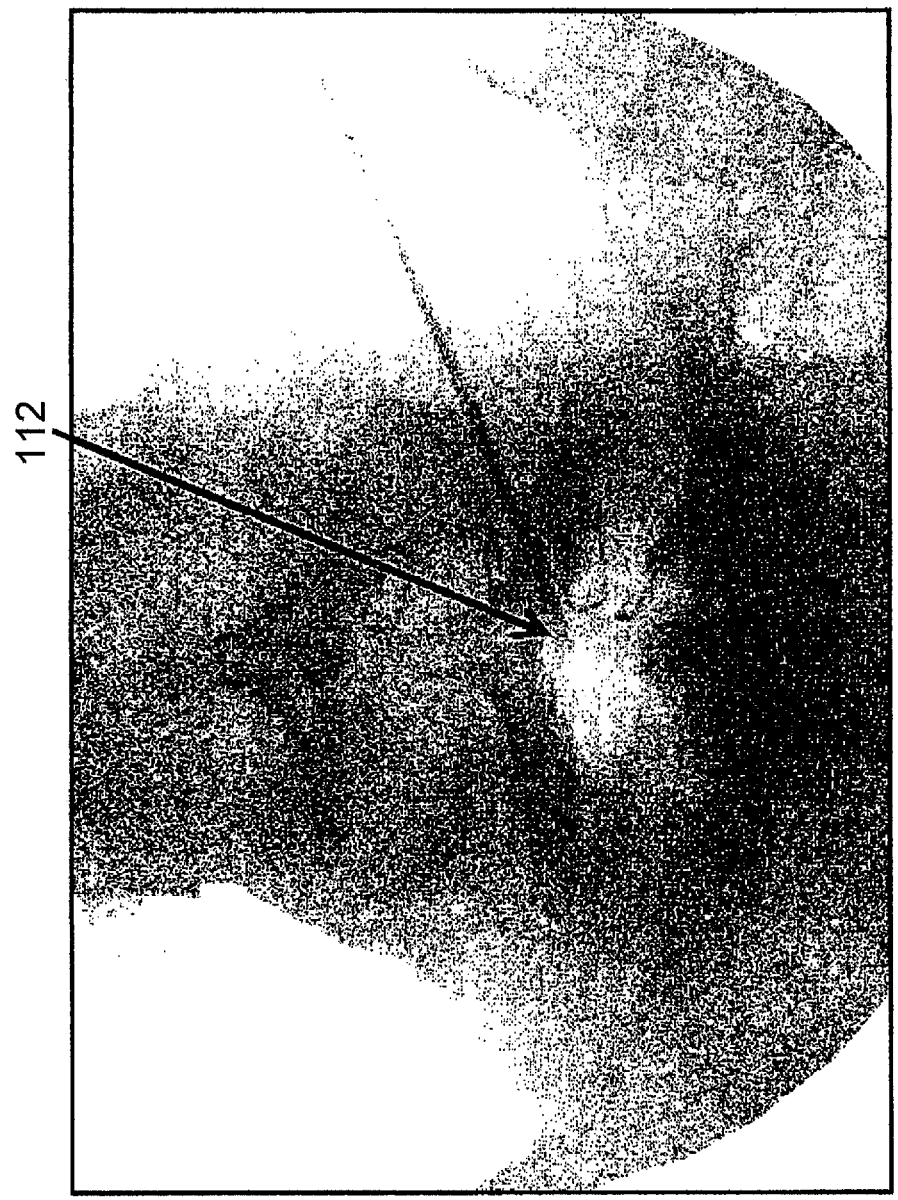

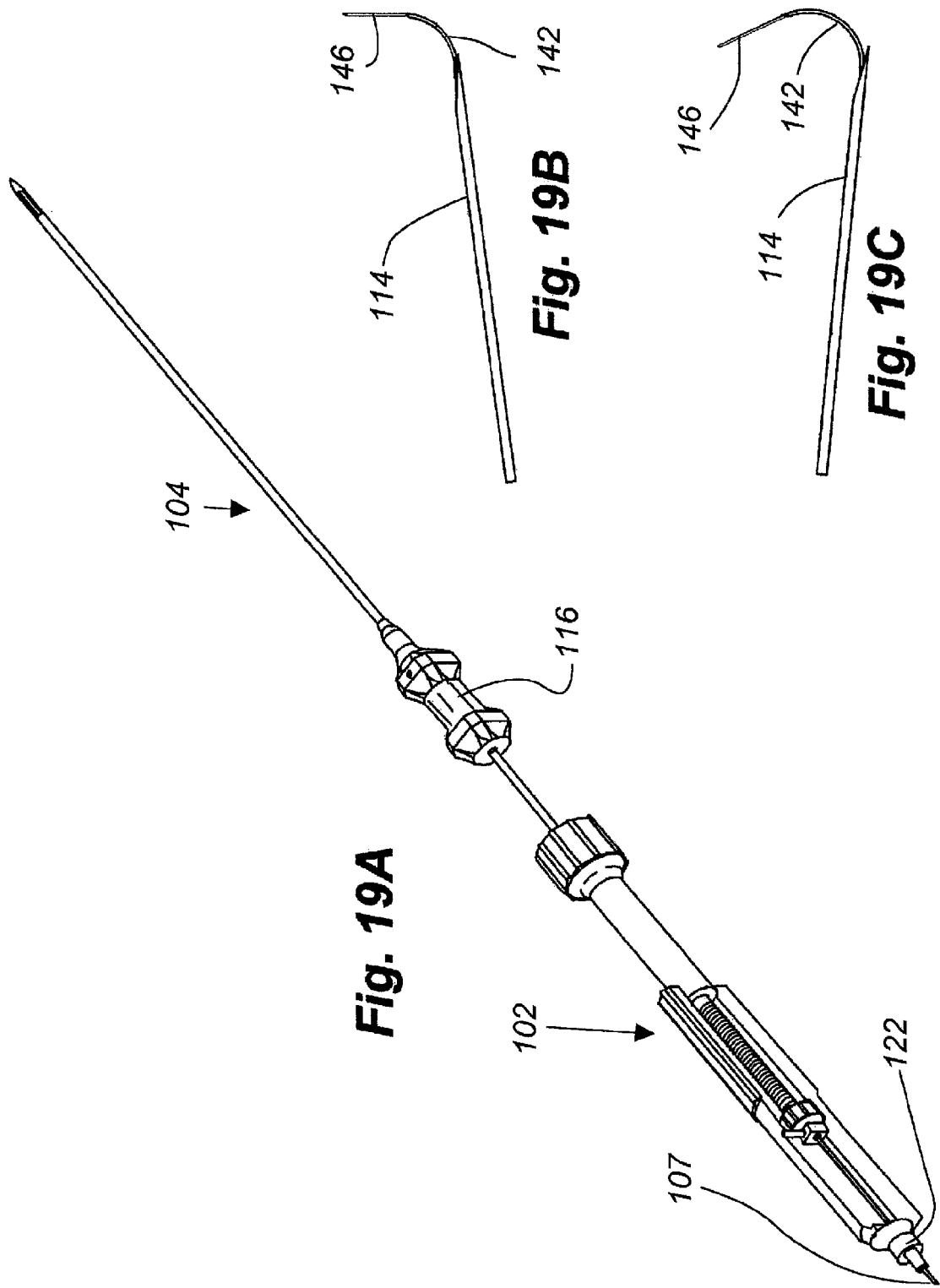

THERAPEUTIC DELIVERY DEVICE

RELATED APPLICATIONS

This application is a non-provisional application of U.S. provisional application Ser. No. 61/258,070, entitled "Therapeutic Delivery Device", filed Nov. 4, 2009; and U.S. provisional application Ser. No. 61/258,314, entitled "Therapeutic Delivery Device", and filed Nov. 5, 2009. Each of these references is incorporated herein by reference in its entirety.

FIELD OF THE INVENTION

The invention generally relates to devices and methods for treatment of damaged tissue, and more particularly, to devices and methods for delivery of therapeutics to specific sites within a damaged tissue, for example, delivery of stem cells to a site within an intervertebral disc.

BACKGROUND OF THE INVENTION

There are particular tissue repair procedures that require the delivery of therapeutics to a target site in a patient's body. Optimally, these repair procedures are performed in a way to minimize damage caused by the repair procedure itself while maximizing the accuracy of placement of the therapeutic in relation to the damage site. Often these repair sites are difficult to reach within a patient's body or are sites in tissue where any disturbance of the surrounding environment can exacerbate and limit the repair process.

In this light, although repair procedures utilizing biologic therapeutics have become more prominent, delivery procedures have not. For example, stem cell therapies directed at cartilage or bone repair are now being widely researched, and procedures developed to maximize the therapeutics capacity for a particular target tissue. However, placement of the stem cells at the target tissue site is generally taken for granted, relying on direct placement of the cells by a surgeon, injection of the cells into the site using an 18 g or 20 g needle, or intravenous infusion of the cells into the patient (relying on the cells inherent capacity to find the correct environment or sheer numbers to gain a foothold at the site). A particular tissue repair site of interest is utilized herein to further illustrate the concepts discussed above, the intervertebral disc.

Intervertebral disc, or disc herein, lie between and separate each vertebra of the spine. Vertebrae within the spine are referred to as being in the cervical, thoracic, lumbar or sacrum regions. Each vertebra comes together to form the spinal column, or spine, which function is to protect the spinal cord, and support the body and head.

Discs make up approximately one fourth of the spine's length, each disc acting as a cushion or shock absorber to protect the vertebrae and other aspects of the spine and brain during movement.

Discs are generally non-vascular, fibrocartilaginous tissue composed of a nucleus pulposus and an annulus fibrosus. The nucleus pulposus is centrally located in the disc and composed of a mucoprotein gel that resists compression and provides the cushion of the disc. The annulus fibrosus is a series of concentric sheets of collagen fibers that surround and enclose the nucleus pulposus. Since the annulus fibrosus surrounds and thereby encloses the nucleus pulposus, the nucleus pulposus is capable of providing an even distribution of pressure across the disc. The annulus fibrosus also provides a tethering point between the disc itself and endplates of adjacent vertebra. Manipulation of the disc environment, annulus or pulposus, can lead to additional damage and can further limit the capability of the disc to be repaired by a therapeutic.

Back pain often results from disruption of one or more disc in a patient's spine. Disc disruption is typically caused by trauma, inflammation, herniation, and/or instability of adjacent vertebral bodies. Conventional therapies address the severity of the disc injury, while attempting to minimize risk and cost to the patient. Often, non-surgical approaches are utilized to treat disc-involved back pain, for example, rest, therapeutic exercise and medications are often a first-line defense in the treatment of back pain. These non-surgical approaches are targeted at a gradual and progressive improvement in symptoms for a patient.

However, in some circumstances a damaged disc requires surgical intervention to facilitate repair of the damaged tissue. Surgical intervention includes invasive and/or minimally invasive procedures, where the type of procedure depends on the severity of the injury or damage. With regard to minimally invasive procedures, a number of endoscope or endoscope-like devices tailored for use in the spine have been developed. For example, disc repair procedures that utilize an endoscope (or other like instrument) include procedures for chemo-nucleolysis, laser directed techniques, and mechanical directed techniques.

Recently, procedures have been proposed for utilizing biologic therapies in disc repair procedures. However, little advancement has been made to facilitate these new therapies, especially with regard to the placement of the therapeutics in the damage site. These procedures require delivery of materials into the disc, for example delivery of stem cells into a site within the disc. Little progress has been made in these stem cell or therapeutic delivery techniques.

As such, there is a need in the art for improved therapeutic delivery devices and methods for the delivery of a therapeutic to a site in a patient. The need in the art requires delivery of therapeutics with high accuracy while minimizing disturbance to the environment of the damage. These devices and methods can be used in the treatment of disc, ligaments, labrum and other like sites.

Against this backdrop the present disclosure is provided.

SUMMARY OF THE INVENTION

Embodiments of the invention provide devices and methods for optimized or facilitated delivery of therapeutics to a target site in a patient in need thereof. For purposes of the present disclosure a "target site," "damaged site," or "target tissue" refers to a site in a patient in need of a biologic therapeutic, typically the site in need of a therapeutic is a site having damage in need of facilitated repair. Illustrative target sites of the invention include disc, ligaments, e.g., ligaments in the upper cervical, posterior longitudinal ligament, facet capsulary ligament, and labrum, e.g., shoulder and/or hip. Embodiments of the invention herein provide a surprising and unexpected improvement over conventional technologies, as will be apparent upon a review of the following disclosure.

In one embodiment, a therapeutic delivery device, or delivery device, is provided that includes a needle assembly. The needle assembly can include either: 1) an introducer needle that internally constrains an advanceable cannula or 2) an introducer needle having the advanceable cannula and further includes an advanceable catheter internally constrained within the cannula. Aspects of the needle assembly allow the cannula and catheter to be independently advanced by a user from the introducer needed to exact distances and with exact arch. The ability to advance the cannula and catheter to specific distances and arches allows for minimal invasiveness of and within the environment of the target site by the delivery device. Needle assembly embodiments herein allow for accurate delivery of therapeutics to target sites in the patient by minimizing damage to the environment around the target site. Aspects of the needle assembly have also been optimized to minimize damage to the therapeutic during the delivery process, for example, minimize damage to stem cells while moving through the delivery device to the target site ensuring high viability of the delivered cells. The catheter and cannula can be produced from memory metal alloys, for example, Nitinol. The introducer needle and cannula can include an alignment marker to ensure proper alignment between the two and provide the user with additional information on positioning of cannula during use.

In another embodiment, a delivery device is provided that includes a handle assembly and a needle assembly. In typical embodiments the handle assembly and needle assembly cooperate to house and deliver the introducer needle, cannula and potentially the catheter to a target site in a patient in need thereof. The arch and distance that the cannula extends from the introducer needle occurs as the cannula is extended out of a pre-positioned introducer needle. As described above, a catheter can be constrained within the cannula and is further advanced out of the cannula once the cannula is positioned within the target site. The handle assembly provides grip convenience to the user during use of the needle assembly. The handle assembly can also include a controller for control of aspects of the needle assembly off of the handle assembly.

In one embodiment the delivery device is optimized for placement of a biologic therapeutic to a target site in a disc. Device embodiments herein are optimized for their capacity to place therapeutics at a specific site of interest in the disc, all the while allowing the health care professional to take a transpedicular approach, for example. Other embodiments of the delivery device are optimized for placement of a biologic therapeutic to a ligament or to a labrum. In some embodiments the delivery device is optimized for placement of cells, for example stem cells, e.g., mesenchymal stem cells, embryonic stem cells, very small embryonic stem cells, blastomere like stem cells, hematopoetic stem cells, annulus fibrosis cells, cord blood cells, other adult stem cells at a target site, including minimizing forces acting on cells during movement through the delivery device. Still other embodiments of the delivery device are optimized for placement of growth factors, glycoaminosglycans, fibrin, fibrin glue, or other substances meant to initiate repair of the annulus.

In another embodiment, a method is provided for optimized delivery of a therapeutic to a target site in a patient in need thereof. The method includes obtaining visual or experimental confirmation of the damage in need of repair, including x-rays, MRI, and the like; inserting an embodiment of the delivery device herein to a position adjacent to or within a distance providing access of the delivery device to the target site (by advancing the tip of the introducer needle to the position); advancing a cannula to a location within or adjacent to the target site, i.e., advancing a particular distance and arch. In some embodiments, a catheter is further advanced from the cannula to a site adjacent or within the target site. In some embodiments confirming that the cannula or catheter is positioned correctly for therapeutic injection into the target site, and injecting the therapeutic through the delivery device to the target site.

In one particular embodiment a method is provided to deliver a therapeutic to a damaged disc. The method includes placing the patient in need of the therapeutic in a prone position; taking x-rays (or other like visual techniques) on the patient to establish a transpedicular approach to the target disc; inserting a delivery device of the present invention via a transpedicular approach in the disc; advancing the tip of the needle in the delivery device to an appropriate position within the disc; advancing a moveable cannula in a predetermined path to position the distal end of the cannula adjacent to the site of damage in the disc; advancing a catheter out of the cannula to the exact location of interest; and injecting the therapeutic through the delivery device into the disc. In some aspects catheter positioning is confirmed prior to therapeutic injection. In other embodiments, a catheter is not required and therapeutics are delivered directly to the disc site through the cannula.

These and various other features as well as advantages which characterize the invention will be apparent from a reading of the following detailed description and a review of the appended claims.

BRIEF DESCRIPTION OF THE DRAWINGS

FIG. 2 is a cross-sectional view along line 2-2 of FIG. 1.

FIG. 3 is an expanded view of one embodiment of the introducer needle, guide cannula and catheter in accordance with the invention.

FIGS. 8, 9 and 10 provide blown-up views of the distal end of the needle assembly, including advancement of the guide cannula and catheter from the introducer needle.

FIGS. 11A, 11B, 12A and 12B provide illustrative delivery device positioning in accordance with embodiments of the present invention. In more detail, FIG. 11A shows a left transpedicular (posterior) approach with the device coursing through the cannula across the nucleus and into the annulus at a site different from the entry point. FIG. 11B shows a left posterior approach whereby the device courses across the annulus into the nucleus. The cannula, cannula and catheter or catheter is then advanced across the nucleus into the annulus.

FIGS. 13, 14A, 14B, 15A, 15B, 16A, 16B, 17A, 17B, and 18 provide x-ray views of illustrative delivery device embodiments tested on cadavers.

FIG. 19A, 19B, and 19C illustrate an alternate view of a delivery device in accordance with embodiments of the present invention.

DETAILED DESCRIPTION OF THE INVENTION

Overview Of Embodiments

Figure 1:
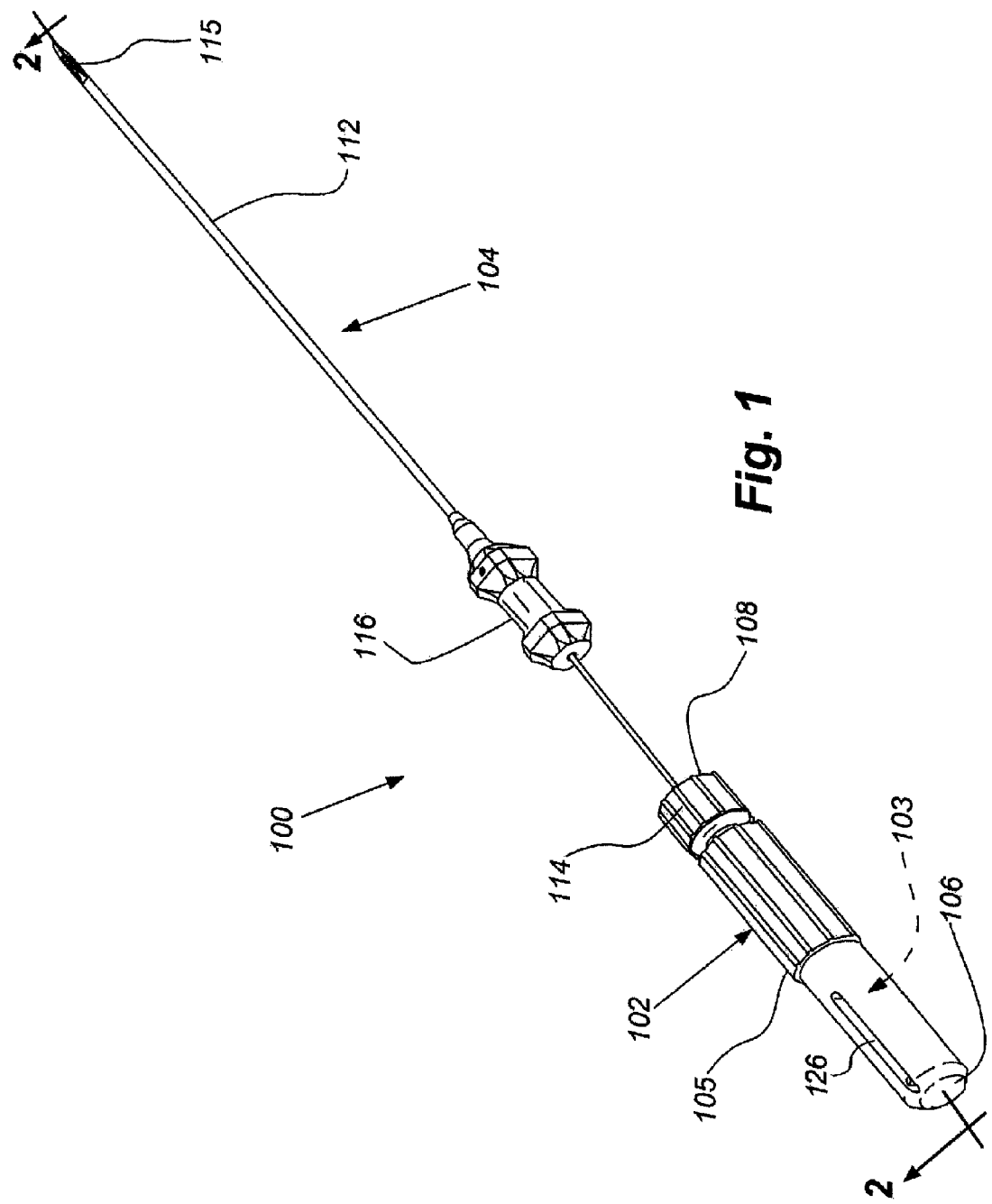
FIG. 1 illustrates a perspective view of a delivery device of the invention, including a handle and needle assemblies.

Embodiments in accordance with the present invention provide devices and methods for delivering biologic therapeutics to a target site in a patient in need thereof. A patient in need thereof for purposes of the present invention refers to a vertebrate and more typically refers to a mammal. In some cases a patient in need thereof is a human, typically a human having a damaged or defective tissue in need of a repair procedure. Target sites in accordance with the present disclosure include: intervertebral disc (disc herein), ligaments, joints, meniscus and labrum. Interverterbral disc targets can be cervical, thoracic and lumbar where both intradiscal and extra-discal approaches can be employed. Joint targets are typically intra-articular: peripheral, cervical, thoracic and lumbar. Labrum targets can be in the shoulder and/or hip. Ligament targets can be upper cervical, posterior longitudinal ligament, facet capsulary ligament and the like.

In one embodiment, the devices and methods described herein are designed for delivery of therapeutic materials to target locations within a target site, for example to a damaged disc where the site is in the posterior disc annulus. Various aspects of the invention provide unexpected improvement over conventional therapeutic delivery apparatuses and methods, both in ability to limit damage to the target site during delivery, and in accuracy of the location that biologics are delivered within the site. Further, embodiments herein have been designed to minimize damage to the therapeutic, for example, designed to deliver viable cells to the site (and to facilitate delivering non-clumped cells). For purposes herein, the term therapeutic is used to include any material that a health care specialist would use to treat a damaged or defective target site, or to immunize a target site. In one embodiment the therapeutic is stem cells and in particular autologous stem cells. Stem cells can be mesenchymal stem cells or other mesenchymal-like stem cells. Therapeutics can also include hormone therapy, vaccines, drugs, tissues, or any other biologic based material that can facilitate repair or improvement in a target site.

In one embodiment, a delivery device is provided that includes a needle assembly, the needle assembly including an elongated, hollow introducer needle having an adjustable cannula therein. The introducer needle (or "needle") has a first end that defines an opening, an elongated cylindrical shaft, and a second end, the second end defining a tip. The tip has an opening so that the openings in the first end and tip allow passage of materials through the needle. The tip is sharp to allow entry of the introducer needle, and thereby the needle assembly, into a patient. Introduction of the introducer needle in a patient is typically based on the location of the target site in need of repair. In one embodiment the introducer needle is a trocar. In another embodiment the introducer needle is a 20 g Sprague needle.

A cannula is internally received through the first end of the introducer needle and extends internally along its shaft. As described further below, the cannula can be advanced in relation to the needle so that a distal end of the cannula can extend through the tip of the needle. In one embodiment, the cannula is made from a memory metal, for example made from a nickel-titanium alloy (Nitinol is one illustrative material). The cannula can be formed to advance out of the needle tip with a pre-determined shape or arch and to a pre-determined distance optimized for locating the distal cannula end in a target location within the patient (determined by the injury site within the patient). Therapeutics are then administered through the cannula. Cannula length and arch can be varied based on the location of the target site, so where a target site is easily accessible to the introducer needle, the cannula may require a very different length and arch than where the target site is inaccessible and distant from the introducer needle.

In one embodiment the introducer needle and cannula are manufactured as a single unit—so the entire introducer needle assembly is provided for a particular use (length and arch of cannula). In this embodiment the introducer needle and guide cannula are integrated as a single unit. In other embodiments the introducer needle is fitted with one of a series of cannula that work for that particular patient target site. In these embodiments, the introducer needle and cannula are manufactured as independent units from each other.

In another embodiment of the invention the needle assembly includes an adjustable catheter (can also be prepared from a memory metal like Nitinol) located in the lumen of the guide cannula. The catheter has the capacity for advancement within and relative to the guide cannula, following the pre-determined length and arch of the extended cannula, and further extending from the distal end of the cannula and advancing with an additional length and arch specific to the catheter. In this aspect, therapeutics are administered through the catheter. Note that various device embodiments can include different cannula and catheters having different lengths and having different pre-shaped arches (forming different arches). Cannula and catheter shapes and lengths are determined by a variety of parameters including: target site, location of the injury in the target site, type of injury, type of therapeutic, size of patient, etc. As discussed above for the introducer needle and cannula, the catheter can be integrated into a needle assembly (a single integrated device) or can be provided separately and mixed and matched with the various length cannula. The combination of cannula and catheter lengths and arches provide an impressive range of potential "throws" that a user can accomplish. For example, a user may only need to deliver a therapeutic to a location close to the entry point of the introducer needle. In such case a short cannula and catheter with minimal arch may accomplish the utility of the delivery device. However, in cases where the target site is difficult to reach and deep within a patient, a longer length cannula and catheter may be required, one that may require up to a 90° arch from the shaft of the introducer needle. For purposes of these inventions the degree arch is determined by the distal end of the cannula or catheter from the shaft of the introducer needle (or straight shafts of the cannula and catheter therein).

In some embodiments the introducer needle and cannula each include an alignment marker for aligning the needle and cannula during use. The alignment marker allows the user to advance the cannula to a particular length and along a particular arch plane. A particular arch plane provides the plane along which the user is advancing the cannula and/or catheter to locate at the target site.

In one embodiment where a catheter advances from a cannula the catheter is aligned so as to maintain the plane of the cannula. In this manner the user need not be concerned that the catheter exits the cannula in a new plane from the cannula.

In another embodiment, a device is provided that includes a needle assembly and a handle assembly. The needle assembly is as described above, with a first end of the assembly attached to and extending from a first or distal end of the handle assembly. The needle assembly and handle assembly are in communication such that movement of the cannula and catheter in the needle assembly can be independently controlled on the handle assembly. In some aspects, therapeutics enter through a port or other opening in the handle assembly, flow through an internal chamber in the handle assembly, into the needle assembly and out the needle assembly to the target site in the patient. Various embodiments allow for the therapeutics to enter the needle assembly via the catheter, or in embodiments that do not include a catheter, through the cannula.

In yet another embodiment, a device is provided that includes a needle assembly, a handle assembly and an interface assembly, the interface assembly positioned between the needle assembly and handle assembly. The interface assembly does not interfere with the handle assembly and control over the needle assembly, but provides the ability to minimize damage to the therapeutics as they enter and exit the delivery device. As discussed further below, the interface assembly is designed to resist cell adherence within, alleviate cell clumping and reducing shearing forces on therapeutics. Additionally, port sites in the interface assembly allow for administration of therapeutics at the interface rather than through the handle assembly. Further, an oscillator may be integrated at the interface assembly to facilitate therapeutic injection into the needle assembly and thereby the damaged target site.

The present invention also provides methods for delivering biologics to a site within a target site of a patient. Methods include insertion of the delivery device needle assembly into or adjacent to a target site, manipulation of the device to maneuver the guide cannula to the defect or adjacent the defect in the target site (including various visualization techniques) and optionally extension of the catheter from the cannula into the site where delivery of therapeutics most beneficial to the patient. Therapeutics are delivered once the catheter is properly positioned relevant to the site of delivery. The method is provided for delivery of therapeutics within the target site, so that a material would be inserted through the catheter into the position that the user intended. In some embodiments, the methods herein include a determination of what length and arch the cannula requires for best results in delivery of therapeutics to the patient. In such embodiments, the method includes modification of a delivery device to include the proper cannula (length and arch) for the target site in a patient.

The device and methods herein are described in more detail in relation to intervertebral disc, but other target uses are contemplated herein. For example, the devices and methods herein can also be utilized in manipulation and/or delivery into kidney, heart, lung, endocrine organs, muscle, ligament, labrum, joints, and the like. As such, the description below is meant as illustrative but not limiting.

Each of these embodiments therefore is described in greater detail below.

Intervertebral Disc

In general, an intervertebral disc has a gelatinous and centrally located nucleus pulposus that resists compression from the weight of the body and provides shock absorptive capabilities to the disc. The gelatinous material of the nucleus pulposus is highly pressurized and surrounded (and entrapped) by a fibrous structure known as the anulus fibrosus. The anulus fibrosus is formed by a series of collagen sheets called Lamellae which form a strong, cartilage-like container.

A posterior longitudinal ligament is located at the anterior aspect of the vertebral canal, which is attached to the outer portion of the anulus fibrosus. Posterior to the disc is the epidural space, a space within which blood vessels and fat tissue are located.

The anulus fibrosus is further defined as having a posterior portion, located between the nucleus pulposis and the posterior longitudinal ligament, and an anterior portion, located toward or adjacent to the body cavity. Within the posterior anulus fibrosus is a vascular or vascularized zone, present to receive and deliver oxygen and nutrients to the disc interior (typically through diffusion). A vascularized transitional zone of the posterior anulus fibrosus disc is also shown, located between the avascular portion of the posterior disc anulus fibrosus and the vascular portion. As such, a disc includes various environments having specialized functions, interruption to any one environment can further exacerbate repair of any other environment.

One aspect of the invention is to provide therapeutic materials for treatment of a disc tear or other damage area within a disc by minimizing trauma to the delivery site. In addition, an aspect of the invention is to accurately locate the delivery of the therapeutic in a position within the disc so as to maximize the therapeutics' capacity to effect repair of the damage. Due to the anatomy of a disc a delivery device is optimal that can minimize entry and damage within the disc tissue and facilitate the delivery of material to a specific location within the disc. Embodiments of the present invention minimize the additional damage to the disc tissue while entering and delivering therapeutics to a target site (note that a target site, as described previously, is the location within the disc that is considered relevant for therapeutic delivery based on the disc injury).

One illustrative aspect of the present invention is to deliver therapeutics, i.e., medicaments and/or cellular therapeutics (including stem cells), to the vascularized zone of the posterior anulus fibrosus. Conventional methodologies, although not designed for delivery of therapeutics, have achieved access to the posterior anulus fibrosis by entering the anterior anulus fibrosus with a probe device and moving the probe through the nucleus pulposis and into the posterior anulus fibrosus. This route and size of the delivery device to the disc, results in additional damage and inaccurate placement of therapeutics. Embodiments of the present invention provide for surprisingly accurate and low damage placement of therapeutics under similar circumstances. Additional illustrative aspects of delivery are provided in FIGS. 11A, 11B, 12A and 12B below. In addition, embodiments herein are provided for entering the posterior annulus fibrosis with a probe that dissects the annular fibers as it is advanced around the annulus to the targeted area (access to the anterior annulus fibrosis is only achieved through a posterior annulus entry with advancement of a catheter in a circumferential path).

Delivery Device

Referring to FIG. 1 (and FIGS. 19A, 19B and 19C for alternative views), an illustrative perspective view of a delivery device 100 in accordance with one embodiment of the present invention is provided. The delivery device 100 incorporates a handle assembly 102 and a needle assembly 104. The handle assembly 102 is typically elongated defining an internal chamber (not shown in FIG. 1) and is ergonomically shaped for manipulation by a user.

Handle assembly embodiments typically include an elongated shaft 105, a first end 106 and a second end 108. In one embodiment the first end 106 defines a port 107 having access into the interior of the handle (see FIGS. 2, 4, 7 and 19A).

Still referring to FIG. 1, the needle assembly 104 includes a hollow introducer needle 112 (for example a trocar or 20 gauge Sprague Needle) for penetration and placement of the needle assembly in the damaged disc. In one embodiment, one or more cannula/catheter members sits constrained within the lumen of the introducer needle. Each of the one or more members is capable of independent advancement within the introducer needle. Advancement of the cannula and/or catheter can be through direct manipulation by a user (move or slide the cannula with respect to introducer needle) or, as described in greater detail below, controlled by an advancement member 114 located on the handle assembly (see FIGS. 2 and 4). Note that aspects of the introducer needle can include a removable stylet 115 to ensure that the cannula and/or catheter does not exit the needle until required by the user. The stylet also prevents the device from being occluded by tissue as the device is being advanced. Generally the introducer needle must define a sufficient diameter to allow for a cannula or catheter having at least a 0.0145 inch diameter and more preferably a 0.015 inch diameter, a 0.0155 inch diameter, a 0.016 inch diameter, a 0.0165 inch diameter, a 0.017 inch diameter, a 0.0175 inch diameter, a 0.018 inch diameter, a 0.0185 inch diameter, a 0.019 inch diameter, a 0.0195 inch diameter, a 0.0205 inch diameter, a 0.021 inch diameter, a 0.0215 inch diameter, 0.022 inch diameter, a 0.0225 diameter, a 0.023 inch diameter, a 0.0235 inch diameter and a 0.024 inch diameter. Larger diameters are contemplated herein, although minimization of tissue disturbance contemplates using a smaller diameter in relation to the functional capacity of the therapeutic, i.e., using a diameter that minimizes tissue disturbance but maximizes, for example, cell viability. The above described diameters provide this benefit.

In some embodiments, an interface, support member or base 116 extends radially from the device, the support member acts as a base to the introducer needle. The support member provides a manipulation site for a health care professional during insertion of the introducer needle into a disc. In some embodiments the support base is ergonomically shaped for optimal use. In other embodiments the support base defines a port to couple the lumen of the needle assembly to an access point for the therapeutic to be administered (not shown).

FIG. 2 shows a cross-sectional view along line 2-2 of FIG. 1. The handle assembly 102 has a generally cylindrical shaped wall 118 that defines a chamber or handle lumen 120 (note that other wall shapes are within the scope of the present invention). A luer lock 122 or other port attachment site is shown at the first end 106 of the handle assembly. As discussed further below, an alternative access point 124 is shown, where the access point can slide within a groove 126 and in relation to the outer wall 128.

An advancement member 130 sits within the handle assembly lumen. The advancement member has a threaded shaft portion 132, a middle portion 134, and an engagement portion 136. A threaded engagement ring 138 is shown integrated into the handle assembly for engagement with the threaded shaft portion of the advancement member. User manipulation of the engagement portion 136 advances the member 130 laterally in relation to the handle wall. Manipulation of 136 advances the member 130 along a rotational axis. Movement of the member 130 is limited by the proximal end 140 of the threaded shaft portion 132. The distances that the member 130 can move in relation to the handle wall is determined by various embodiments of the delivery device and length and extension required for the cannula. Note that in one embodiment, port 124 moves with the advancement member 130 within groove 126 of the handle wall.

FIG. 3 shows a blow-up cross-sectional view of one embodiment of the needle assembly 104. An introducer needle 112 constrains an internally located guide cannula 142. A proximal end 144 of the guide cannula is attached (either fixedly or removable are contemplated) to the advancement member 130 (not shown in FIG. 3). In some embodiments, a catheter 146 sits within the lumen of the cannula. The cannula and catheter are configured to allow for relative movement relative to each other and to the introducer needle. A bore or opening 148 in the introducer needle provides an egress point for the cannula (as moved or extended laterally by the advancement member). Note that some embodiments have the catheter extending from the advancement member or advanced through the proximal end of the cannula 144 (see FIG. 3). Where the catheter is positioned on the advancement member, a lumen or passage in the handle assembly will allow transport of the therapeutics from the handle entry point to the advancement member.

Although not shown in the figures, needle assembly embodiments, having no handle assembly, can be utilized by a user where the cannula is directly advanced by the user through and out of the introducer needle. In such aspects the cannula could be griped by the user and moved through and out the tip of the introducer needle to the predetermined location for therapeutic delivery. A catheter could also be manually advanced through the cannula.

Figure 4:
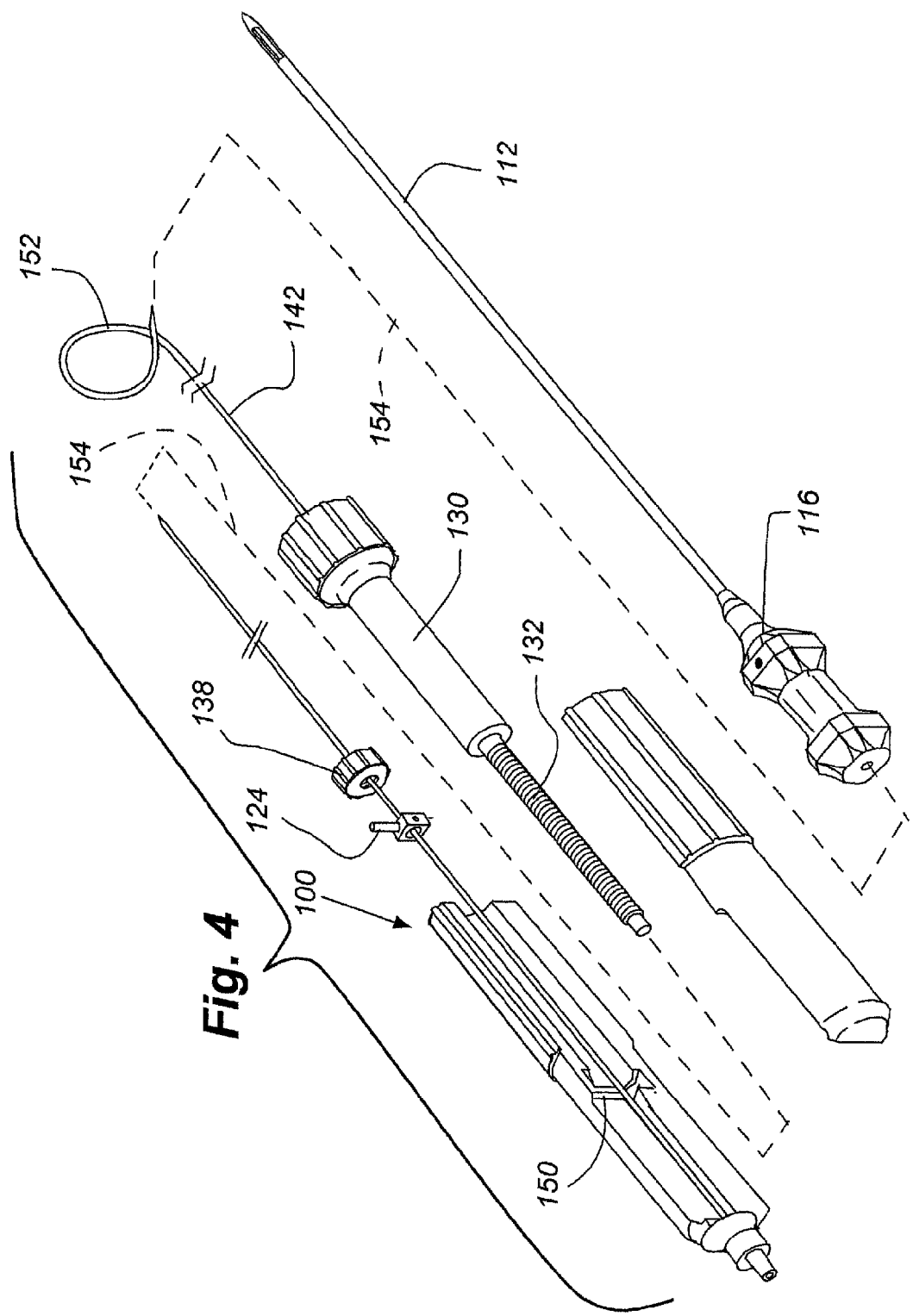
FIG. 4 an exploded view of a delivery device of the invention, including the handle assembly and needle assembly in accordance with the present invention.

FIG. 4 is an exploded view of an illustrative delivery device 100 in accordance with the present invention. The advancement member 130 with cannula 142 engages the handle ring 138. The handle ring 138 is set internally within a pair of internally extending flanges 150 of the handle wall. The set handle ring provides a point against which the advancement ring is fed (particularly the threaded shaft portion). The movement of the advancement member moves the guide cannula 142 in relation to the introducer needle 112. As the advancement member is manipulated, the cannula advances through the introducer needle and, once the distal end of the cannula exits the needle, a pre-formed shape is taken 152 (the preformed shape is constrained until exit by the walls of the introducer needle). A catheter is shown as it extends from a port entry site and through the advancement member, and thereby through the cannula. Dashed lines 154 show the containment pattern for both the catheter and cannula within the handle and needle assemblies.

In another embodiment of the advancement member (not shown), the advancement member has a distal and proximal end. Advancement of both the guide cannula and catheter is achieved through standard screw drives. A distal screw has both internal and external threads. Advancement of the guide cannula results from rotation of a distal housing by the user relative to the introducer needle, causing advancement distally of the distal screw drive by virtue of the outer threads. Advancement of the catheter results from rotation of the proximal housing by the user, wherein the proximal screw drive will screw into the internal threads of the distal screw drive.

In another embodiment of the invention, an alignment marker is provided on each of the introducer needle and cannula to ensure that user advances the cannula to a correct distance and on a correct plane (control arch). Alignment markers can be a visible line (red, black, etc) or elevation that allows correct alignment of the introducer needle and cannula. Alignment markers can include angular and length information relative to the shaft of the introducer needle. In one embodiment the alignment marker is a radio-opaque marker located on each of the introducer needle, guide cannula and catheter. The radio-opaque marker ensures the proper advancement of the guide cannula and catheter in the same plane.

Embodiments of the invention include a number of different shaped cannulas and catheters. Variation in cannula and catheter length and arch are meant to cover a multitude of different possibilities. Length and arch are generally determined by the patient's body habitus, the target site in need of repair, the location of the damage in the target site, and other like considerations. Embodiments herein include pre-fabricated delivery device that include a particular length and arch for a cannula and catheter. The arch shape being maintained by a memory alloy. So for example, a cannula that can extend from 0.1 inch to 4.0 inches from the introducer needle at a 15 to 180° angle from the introducer needle shaft (determined from the distal end of the advanced cannula or catheter). A user would have access to a variety of delivery devices that cover a multitude of length and arch requirements. Embodiments herein also include delivery device where a particular length and arch cannula/catheter can be replaced into the device, thereby limiting the number of delivery device a user requires to one, with a number of cannula and catheter options to insert dependent on any particular patient's need.

Figure 6:
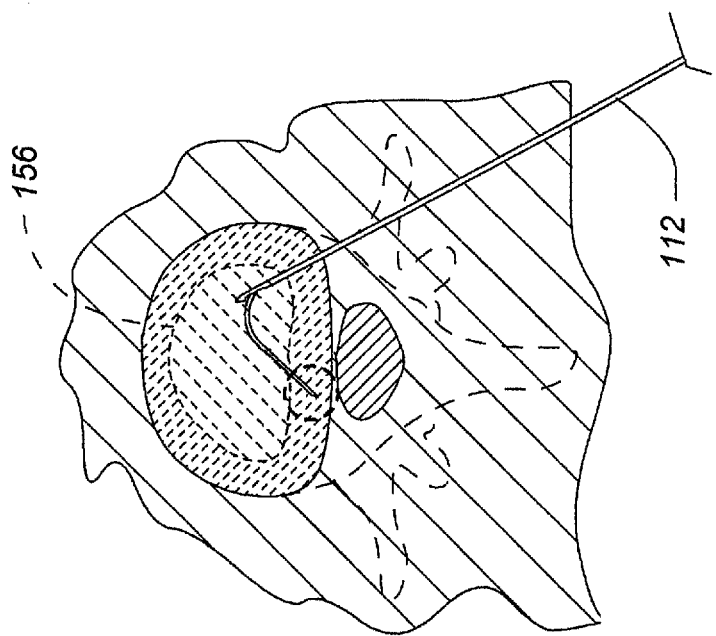
FIGS. 5 and 6 illustrate placement of the delivery device in a disc in accordance with the present invention.
Figure 5:
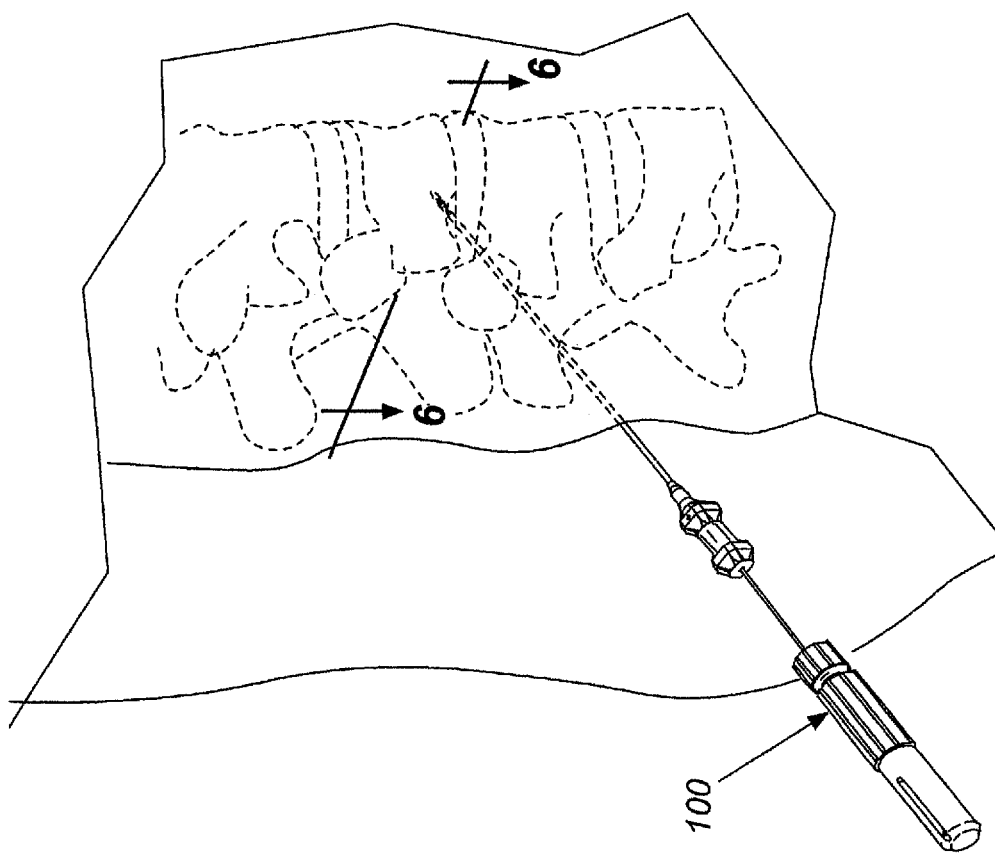

FIGS. 5 and 6 provide a view of a delivery device 100 positioned to treat a damaged disc 156 in accordance with embodiments herein. For example, treatment options include but are not limited to: annular placement, transannular and into the nucleus, and transannular, into the nucleus and then back into the annulus as a site different than the entry site (see FIG. 6). Introducer needle placement and cannula advancement into the disc provides a pre-shaped or pre-determined pathway for treating a disc. Typically, a health care professional makes a determination prior to a procedure for which shape (length and arch) cannula (and where appropriate, catheter) is most beneficial to the patient.

Figure 7:
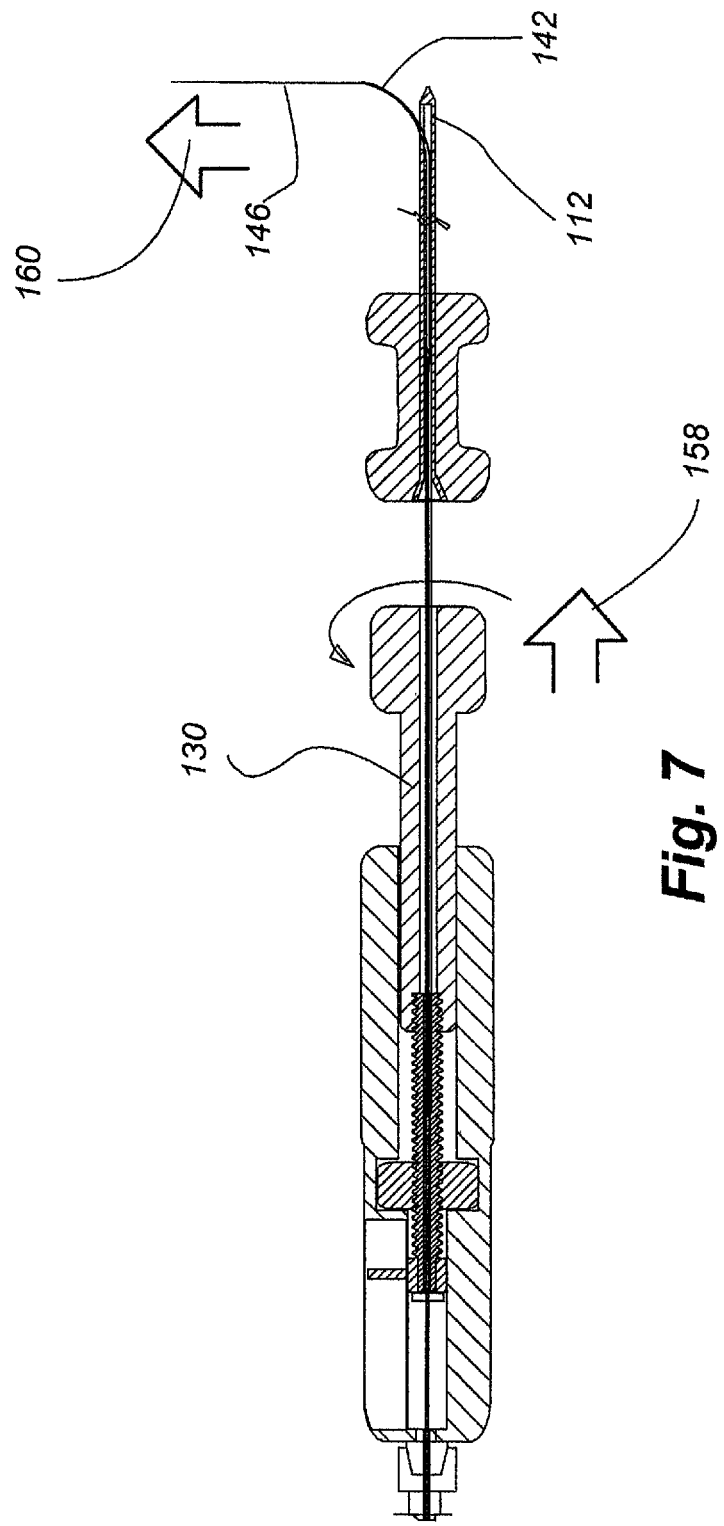
FIG. 7 is a longitudinal cross-sectional view of a delivery device, showing advancement of the guide cannula within and out of the distal end of the introducer needle.

FIG. 7 illustrates advancement of the guide cannula 142 and catheter 146 from the distal end of the introducer needle 112. In one embodiment, turning of the advancement member 130 extends the member along the path of arrow 158. As the advancement member engages the handle ring, it moves laterally away from the handle wall. The cannula attached to the advancement member is then advanced through the bore at the tip of the introducer needle, allowing the cannula to form its pre-determined shape (based on the memory metal alloy). The extension of the cannula can be visualized via arrow 160. In some embodiments there is no catheter, and therapeutics can be delivered through the handle assembly, through the advancement member and through the cannula, and ultimately be extruded through the distal end of the cannula. In other embodiments, as shown in FIG. 7, a catheter is constrained within the cannula. The catheter has additional length compared to the cannula and will continue to advance out the distal end of the cannula as the advancement member is moved laterally away from the handle wall. Other advancement controls for the cannula and catheter are contemplated and are within the scope of the present invention.

Figure 8:
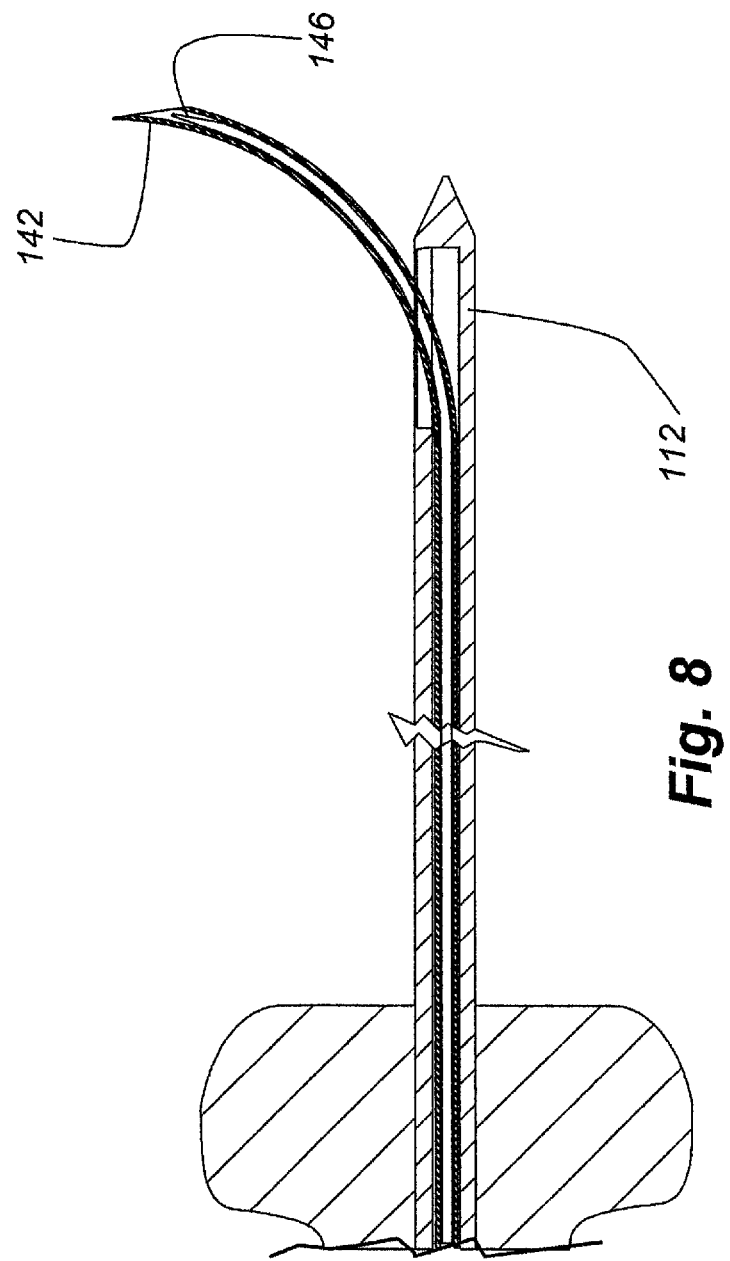
Figure 9:
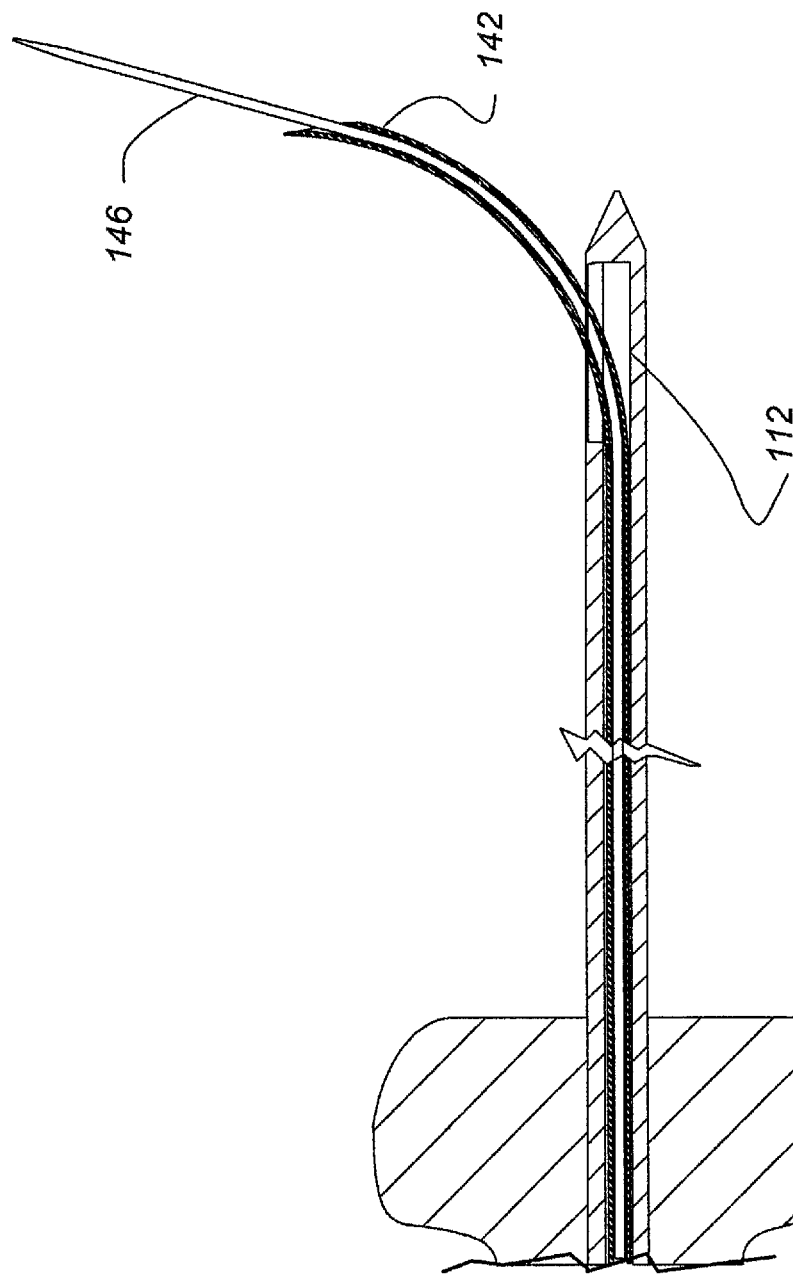

FIGS. 8, 9 and 10 show several pre-shaped or pre-determined shapes that the cannula can take after full extension from the introducer needle. These shapes minimize disruption of the tissue anatomy and are selected at the discretion of the health care user. Different shaped distal ends of the cannula can be used for delivery of therapeutics at different sites within the tissue. Note that a tapered end of the cannula can be utilized to facilitate movement through the disc tissue. The tapered direction would correspond to the pre-determined direction that the cannula end would move.

FIGS. 11A, 11B, 12A and 12B show relative positioning of a needle assembly of the invention in relation to a damaged disc. FIG. 11A shows the delivery device entering the left posterior approach and deployed to treat a right posterior lateral disc tear (note that the catheter in this example would typically be used only to the back of the disc annulus, not beyond as is shown). FIG. 11B shows a delivery device entering the left posterior approach and deployed to treat a right lateral disc tear. FIG. 12A illustrates the delivery device entering the left posterior approach and deployed to treat a posterior disc tear just left to mid-line. Note in this example, the health care professional has chosen not to insert the catheter to reach the lesion. Finally, in FIG. 12B the delivery device enters the left posterior approach and is deployed to treat a left posterior disc tear. Note in this example, the health care professional has chosen not to insert the catheter to reach the lesion. Note that the device can be used to insert into the posterior annulus only (not shown).

Alternative embodiments herein include a delivery device where the handle assembly and needle assembly are separate. Prior to insertion of the handle assembly onto the needle assembly base, an interface adapter (not shown) is provided. The interface adapter is inserted between the handle and needle assemblies in order to reduce sheering forces on the therapeutics. This would be particularly useful when the therapeutic is a cell based biologic. In some embodiments the interface adapter is prepared from a material that: 1) resists the cells from adhering to surface; 2) resists the cells or other therapeutic clumping; and 3) reduces the shearing forces on injectate which can be achieved through—a) a tapered reduction in internal diameter from the proximal port (connected to the handle) down to the distal port (connected to the introducer needle), b) side-port which allows for injection of therapeutics which will decrease concentration of cells, reduce clumping and reduce shear forces and c) side-port which will allow for an automated device to be connect, where the automated device will have the potential to inject substances in a automated, controlled fashion with the ability to regulate injection rates and injection forces. In some aspects the automated device can include an oscillator for gently agitating therapeutics.

After extensive testing (see Examples herein), cannula and catheter materials have been identified for maximal utility. Cannula and catheters of the invention include shape memory metals and shape memory polymers. Typical embodiments herein are made from nickel and titanium alloy, e.g., nitinol, and other like materials. The unexpected and surprising findings disclosed in Examples 1-4 show that nitinol effects viability of cells only to the same extent as does polyether ether ketone (PEEK). Note that PEEK is one of the conventional materials used in the medical device and biologics industries for contact with and manipulation of biologic materials. As such, use of nitinol based materials herein have little or no adverse effect on delivery of biologic therapeutics, while providing the benefit of shape memory and super elasticity.

Cannula and catheter embodiments herein can illustratively have the following parameters: loading plateau stress at 3% strain can range from 300-600 MPa/72,500 psi; tensile strength of 1,250 MPa/181,000 psi; maximum residual elongation after 8% strain ranges from 0.4 to 0.6% and minimum elongation to failure of 10% (strain is deformation in the material, and is shown as a %; tensile strength is shown as a load per cross sectional area and applies to both cannula and catheter). Embodiments herein, when constructed from shape memory metals, will always be used in the austenite phase.

There are a number of different cannula embodiments that illustrate a variety of different cannula arches and lengths. Cannula embodiments can be produced having a 15°, 30°, 45°, 60°, 75°, 90°, 105°, 120°, 135°, 150°, 165°, and 180° angle between the shaft of the cannula (or introducer needle) and the distal end of the cannula (other angles are also contemplated to be within the scope of the present invention). In addition, each cannula showing an arch can have an arch region or length of the cannuala that extends 0.25 inches, 0.5 inches, 0.75 inches, 1.0 inches, 1.25 inches, 1.5 inches, 1.75 inches, 2.0 inches, 2.25 inches, 2.5 inches, 2.75 inches, 3.0 inches, 3.25 inches, 3.5 inches, 3.75 inches and 4.0 inches (from the introducer needle). Other arch angles and lengths are also contemplated herein and are considered within the scope of the present invention. The combination of arch angle and arch length provides the health care professional with a multitude of options to both minimize disturbances in the tissue site environment and, where required, to go around or avoid environments completely (for example where the site is located next to or within a particularly delicate location).

Delivery Methods

Methods of the invention include therapeutic delivery of biologics to a target site in accordance with the present invention. The method includes obtaining visual or experimental confirmation of the damage in need of repair (and establish the appropriate disc level), including x-rays, MRI, and the like; inserting an embodiment of the delivery device herein to a position adjacent to or within a distance providing access of the delivery device to the target site (by advancing the tip of the introducer needle to the position); advancing a cannula to a location within or adjacent to the target site, i.e., advancing a particular distance and arch. In some embodiments, a catheter is further advanced from the cannula to a site adjacent or within the target site. In some embodiments confirming that the cannula or catheter is positioned correctly for therapeutic injection into the target site, and injecting the therapeutic through the delivery device to the target site.

Note that an alternative use is that the device can be used for ipsilateral lesion, for example a left sided transpedicular approach for a left sided disc lesion.

In one embodiment, an initially a determination is made by a health care professional that the treatment regiments of the present invention would be useful in facilitating repair of one or more of the patient's disc. In one embodiment, a patient in need of treatment is prepared for surgery using standard pre-operative techniques. The patient is then placed on an x-ray table in the prone position, i.e., face down on the table. A sterility preparation is performed on the patient to limit opportunity for infection. A series of intermittent x-rays are performed on the patient to establish a transpedicular approach to the damaged disc(s). Where the defect is located on the left side of a disc a right transpedicular approach is used, and where the defect is located on the right side of the disc a left transpedicular approach is utilized.

The health care professional then places a tip of a needle of a needle assembly in the defective disc utilizing the above mentioned transpedicular approach with intermittent x-ray. In one embodiment, a cannula from the needle assembly is advanced in a predetermined shape into the damaged disc to facilitate placement of the cannula (and in some embodiments the catheter) into the area of damaged tissue. In some method embodiments a catheter is not provided, rather the therapeutics are delivered directly through the cannula. In another embodiment the needle is straight at its distal end. The needle has a lumen through which the catheter and subsequent stylets or trochars are advanced. The lumen can be a standard size lumen for a trocar or other endoscopic like device.

Once the health care professional has positioned the needle assembly, a stylet from the introducer needle is removed and a steerable catheter is advanced through the introducer needle into the nucleus pulposis (or other site within the disc). The health care professional then navigates the cannula and catheter to the site of damage in the disc which requires traversing from the disc nucleus pulposis to the posterior annulus fibrosus (for example). In one embodiment, the needle assembly provides an alignment marker for ensuring that advancement is along the correct plane.

In typical embodiments, the health care profession confirms the placement of the catheter in the correct region of the posterior annulus fibrosus. Positioning confirmation can be tactile and/or via x-ray. In some cases the stylet within the catheter is removed and a small amount of contrast is injected to confirm placement at or within the target location in the posterior annulus fibrosus. In such cases an annulogram is performed to confirm location and to document for future use.

As discussed herein, the catheter of the invention can have one or more different configurations based on the length and shape of the cannula. Cannula configurations are generally used for delivery of target therapeutics to the target site in the defective disc. In one embodiment the cannula has been optimized for delivery of stem cells to the site in which the cannula has been positioned. Cannula shapes are pre-determined using shape memory metals (alloys) and are utilized based on the shape and site of injury, size of disc, and other parameters determined by the user.

The health care professional obtains the biologics for delivery where delivery is through the above described methods. In one embodiment the biologic is stem cells and in particular autologous mesenchymal stem cells. The health care professional injects the biologic into the delivery device and ultimately to the catheter, which has a lumen, with resultant implantation of the stem cells into the target region of the posterior annulus fibrosis (for example). Note that the injection of a biologic is performed over a period of time sufficient to inject an appropriate number of cells or growth factor (in the absence of causing damage to the cells or biologic). Where the biologic is an amount of expanded autologous stem cells, injection should be performed over a period sufficient to allow for injection but minimize damage to the cells. Once the health care professional is satisfied that the correct type and amount of biologic has been injected, the catheter is removed. Note that in general, therapeutic ejection rates are from 5 µl/min to 50,0000 µl/min.

Once the catheter has been removed the health care professional withdrawals the needle from the site and through the nucleus pulposis to the superior, posterior aspect of the targeted neural foramen. In one embodiment an amount of contrast is injected or inserted into the device is to confirm the flow into the epidural space. Finally, the health care professional takes from about 5 to 15 cc of the patient's blood, and more particularly about 10 cc of the patient's blood, and injects or inserts the blood into the introducer needle at this site. The patient's blood provides an epidural blood patch and thereby minimizes bleeding and inflammation into the site of repair (as well as leakage from the nucleus and annulus). As such, the blood patch acts to provide a sealant where the introducer punctured the annulus fibrosus and prevents leakage of the injected biologics from the posterior annulus fibrosus.

Mesenchymal Stem Cells as a Therapeutic

Mesenchymal stem cells (MSCs) are pluripotent blast or embryonic-like cells located in blood, bone marrow, dermis and periosteum. In general these cells are capable of renewing themselves over extended periods of time as well as, under various environmental conditions, differentiating into cartilage, bone and other connective tissue. Recently, various investigators have researched the potential for using these cells to repair or regenerate target tissues, e.g., bone, cartilage, cardiac muscle, etc. In this manner MSCs have been reported to have regenerative capabilities in a number of animal models. See Acosta et al. (2005) Neurosurg Focus 19(3):E4; Barry (2003) Novartis Found Symp. 249:86-102, 170-4, 239-41; Brisby et al. (2004) Orthop Clin. North Am. 35(1):85-89; Buckwalter and Mankin (1998) Instr Course Lect. 47:487-504; Caplan (1991) J Orthop Res. 9(5):641-650. Each of these references is incorporated by reference in their entirety for all purposes.

The present inventor, and others, has proffered potential therapeutic uses for delivery of stem cells, and in particular, mesenchymal stem cells, to a damaged disc (see U.S. patent application Ser. No. 11/773,774 and U.S. patent application Ser. No. 12/161,911, each of which is incorporated herein by reference for all purposes). Delivery of these cells to a site in a disc in a manner that minimizes additional damage to the disc's integrity is a concern for the health care industry. Embodiments of the present invention, including device and methods, optimize delivery of these highly useful therapeutic tools to the disc. Embodiments herein provide an unexpected improvement over conventional stem cell delivery procedures.

Other Therapeutic Therapies for Disc Repair

Embodiments of the present invention include positioning of biologics in repair sites of defective or damaged disc. Embodiments of the present invention are useful for delivery of biologic therapeutics to a specific site within a damaged disc, for example, delivery of growth factors, inflammatory inhibitors and/or intracellular regulatory proteins for treatment of degenerative disc disease. Delivery of biologics to a damaged disc using conventional methodologies can be problematic, especially where intrusion into the disc is required. Embodiments as described herein provide an unexpected improvement over conventional apparatus and methods for delivery of biologic materials to a specific site within a damaged disc.

Additional embodiments of the present invention also include positioning non-stem cell biologics into non-disc target sites. For example, vaccines, collagen, growth factors, anti-inflammatory agents, and other know therapeutics can be delivered via the delivery device of the present invention.

EXAMPLES

Example 1

Cadaver Testing Utilizing Several Delivery Device Embodiments

Figure 13:
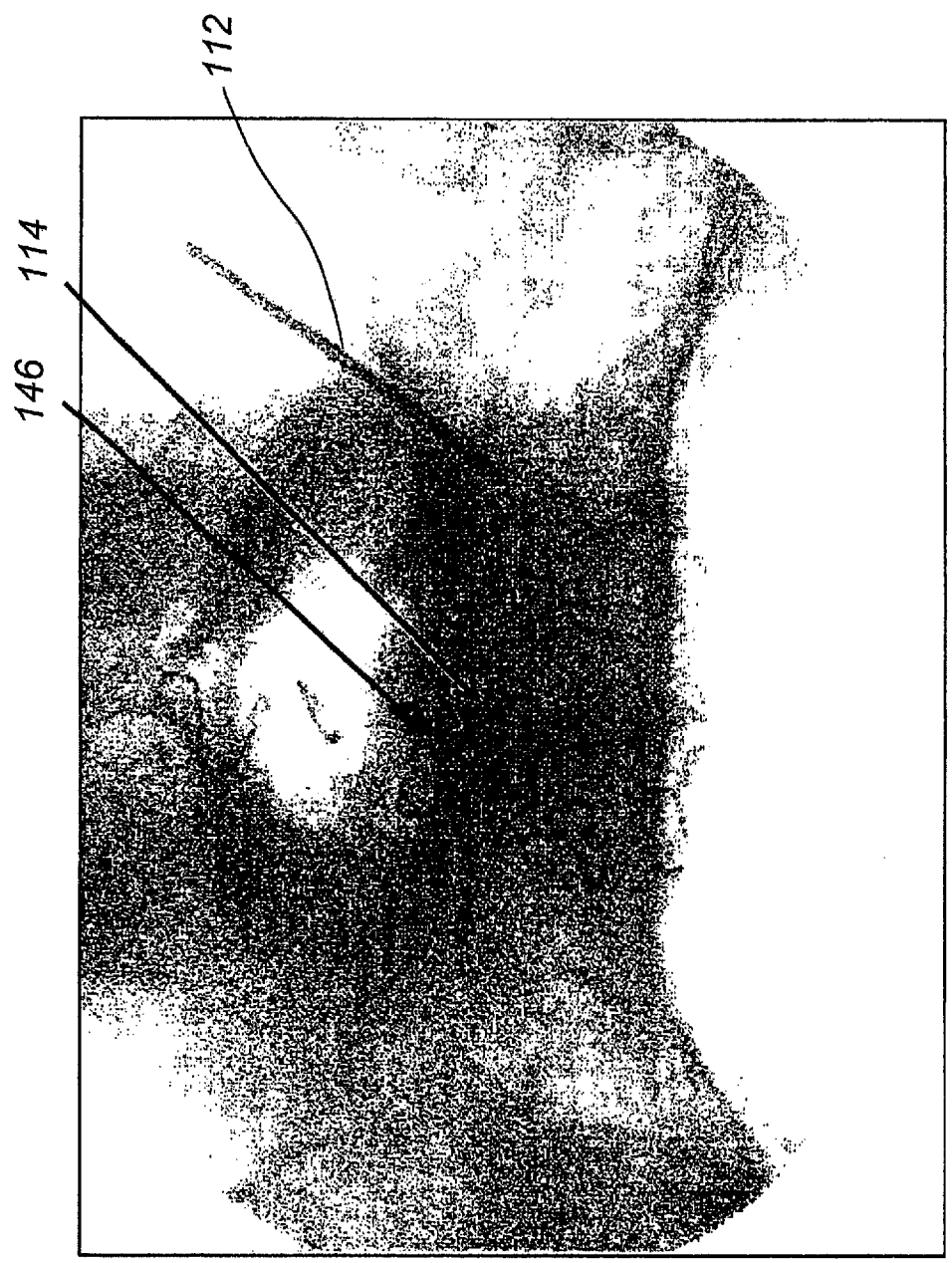
Figure 14A:
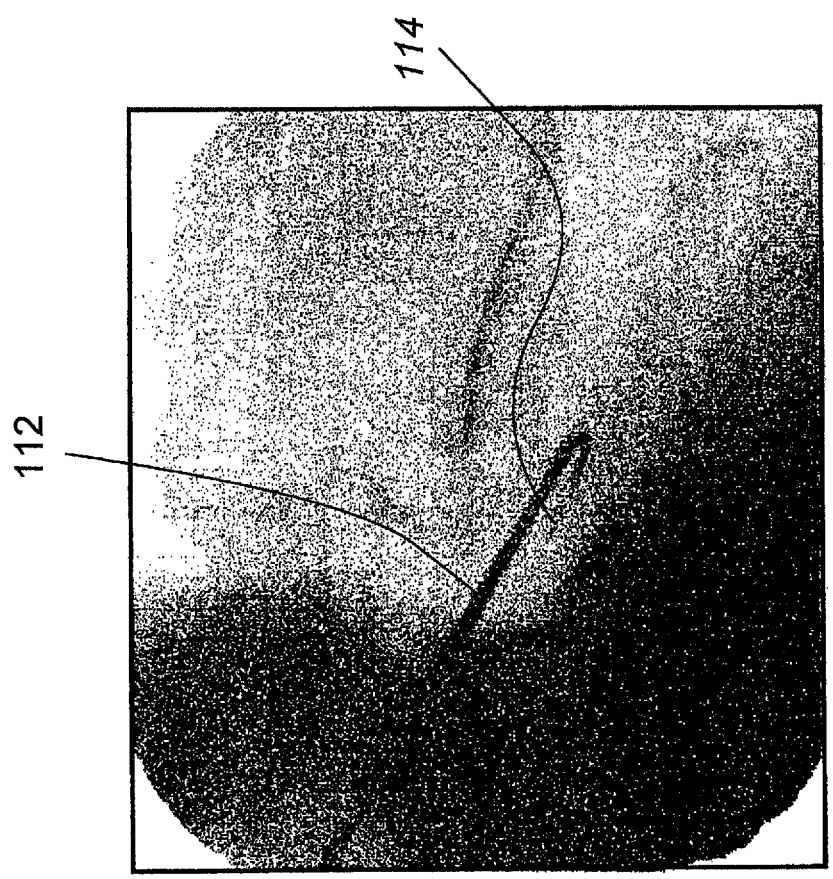
Figure 14B:
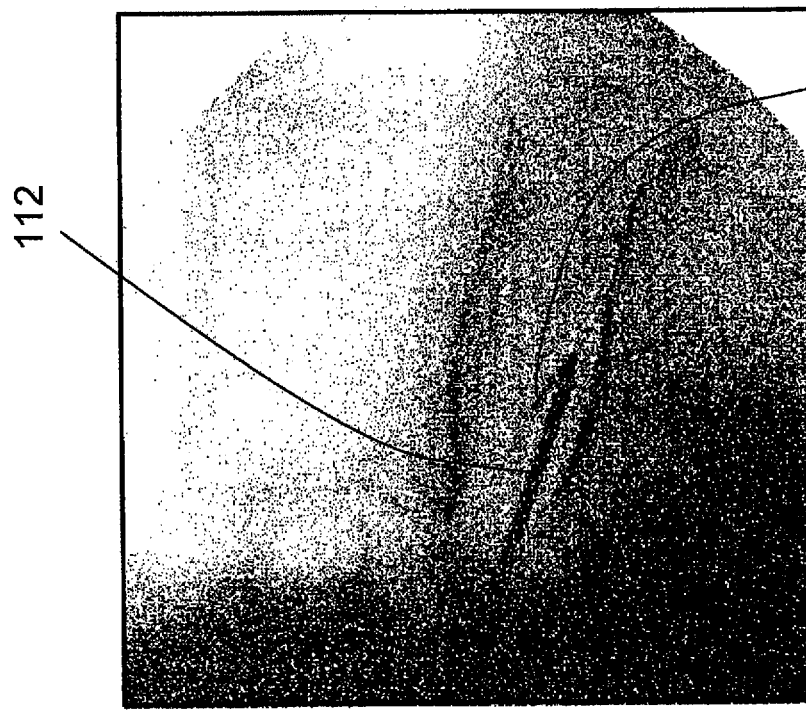
Figure 15B:
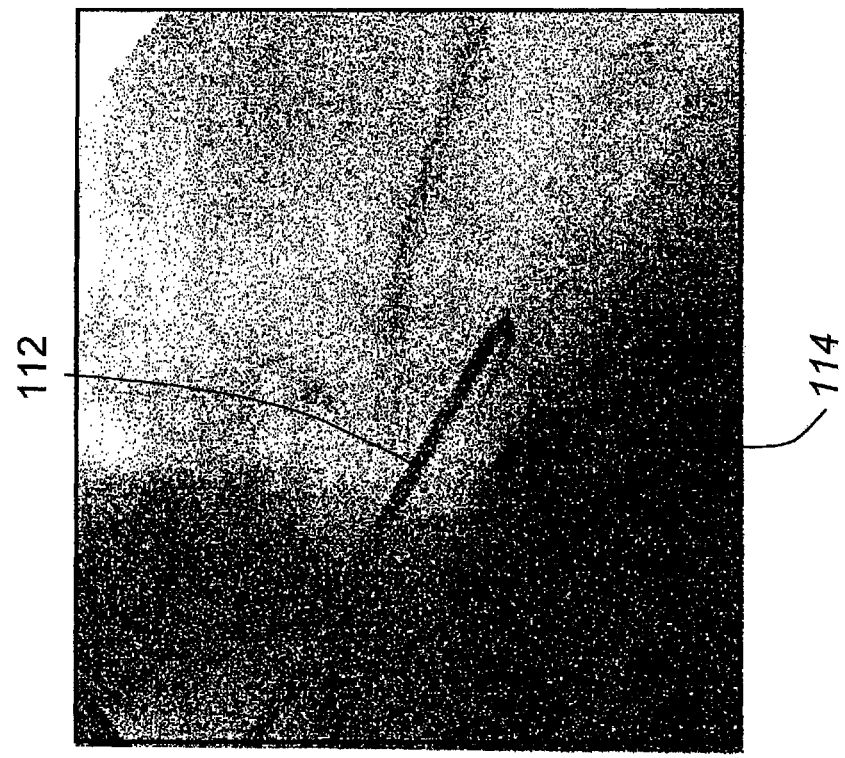
Figure 15A:
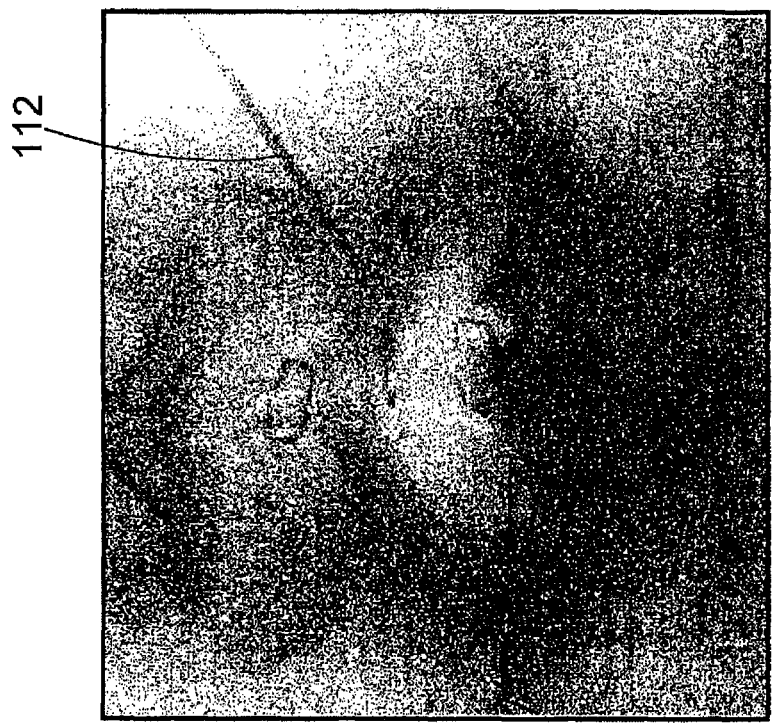
Figure 16B:
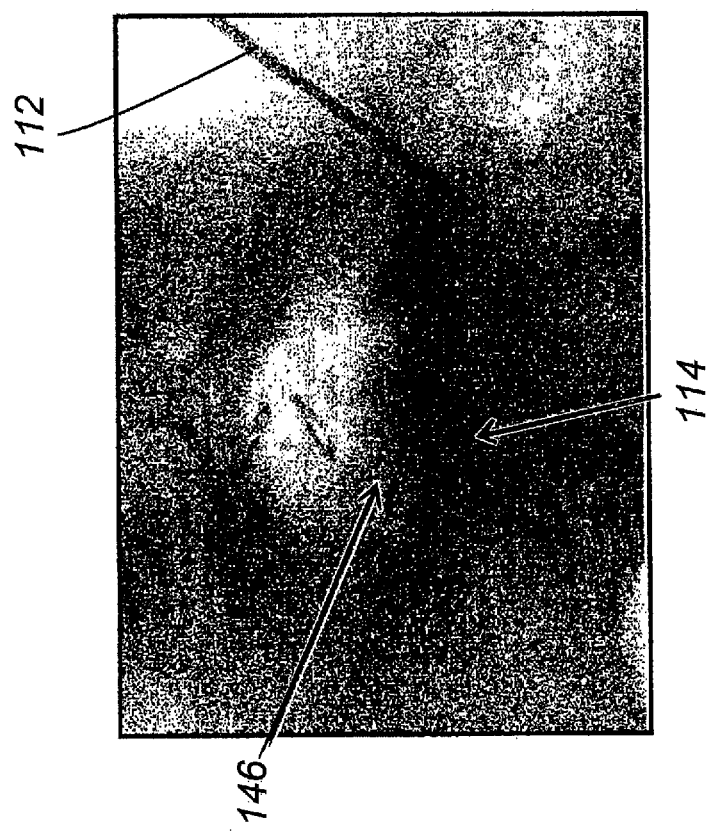
Figure 16A:
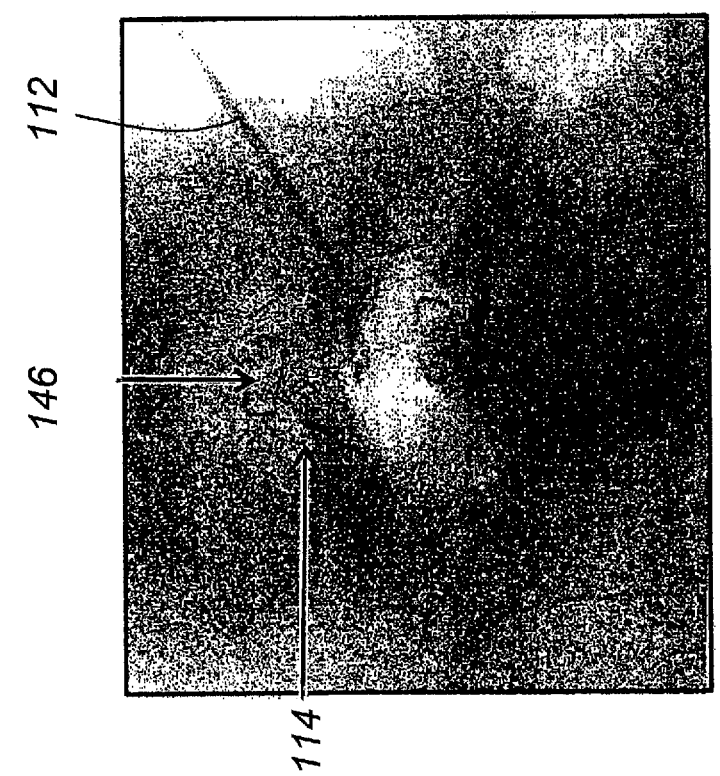
Figure 17B:
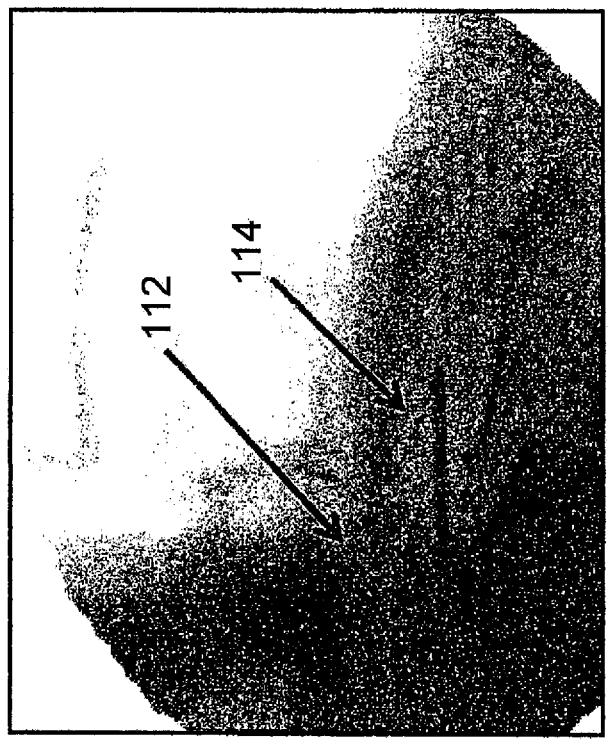
Figure 17A:
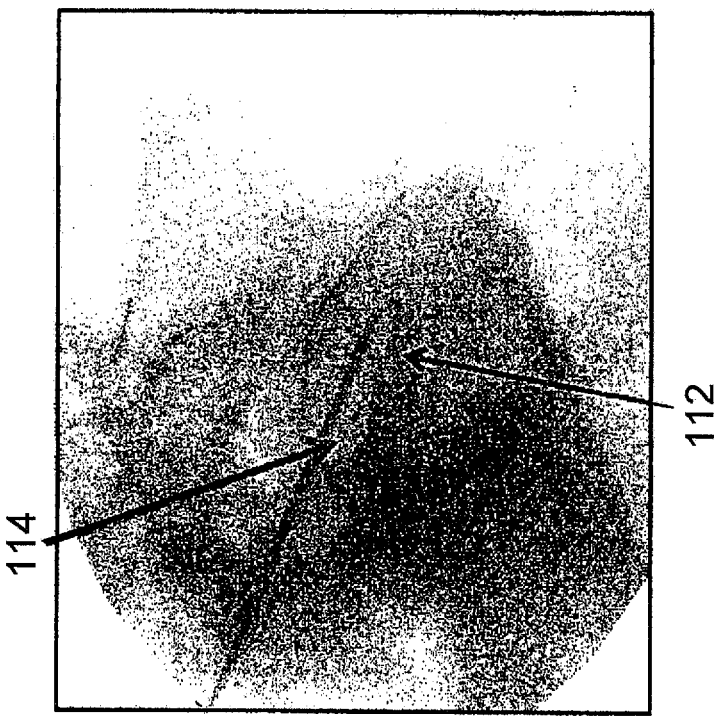

FIGS. 13, 14A and B, 15A and B, 16A and B, 17A and B and 18 provide illustrative visualization of a delivery device embodiment of the invention in use during cadaver testing. X-rays were taken of variously positioned device embodiments in accordance with the present invention. FIG. 13 shows a guide cannula fully deployed with catheter advanced to annular-nucleus interface; FIG. 14A shows a L5/S1 Lateral, with rotation of bevel up resulting in cannula and catheter driving cephalad and FIG. 14B shows L5/S1 Lateral, with rotation of bevel down resulting in cannula and catheter driving caudally; FIG. 15A shows L5/S1, rotation of bevel up resulting in cannula and catheter driving cephalad and FIG. 15B shows L5/S1, rotation of bevel down resulting in cannula and catheter driving caudally; FIG. 16A shows an end table view where the arrow points to a catheter exiting a guide cannula and FIG. 16B shows a end table view where the arrow points to a catheter exiting a guide cannula; FIG. 17A shows a L5/S1 lateral with rotation of bevel and caudal direction, the cannula extending to NP/AF interface; FIG. 17B shows L5/S1 lateral with rotation of bevel and cephalad direction, the cannula extending beyond NP/AF interface; and FIG. 18 shows an L5/S1 end of table view of a guide cannula not sufficiently deployed so that the catheter exits in a lateral angle.

Example 2

Stem Cells Viability Based on Cannula Composition and Diameter

In order to further ascertain utility of various embodiments of the delivery device, mesenchymal stem cell viability was determined before and after injection through a Nitinol guide cannula.

A guide cannula constructed from Nitinol having a 0.024 inch diameter shows little adverse effect on cell viability as cells were injected/passed through the length of the cannula. Cell viability was similar to that of cells injected/passed through a stainless steel 18 g needle (0.049 inch diameter).

In particular, cultured mesenchymal stem cells were harvested and viability verified by testing a sample via a trypan blue exclusion test. Cells were then broken into two groups for injection through either the 18 g stainless steel needle or the Nitinol guide cannula. After injection, cell viability was re-determined based on how many viable cells were present after exit from either the needle or the cannula. There were $2.55 \times 10^6$ viable cells after injection through the 18 g needle and $2.75 \times 10^6$ viable cells after injection through the Nitinol guide cannula.

This Example illustrates the capability of a Nitinol guide cannula to support cell viability in a manner similar to or better than an 18 g stainless steel needle. In addition, the data indicates that few if any cells were lost by injection through the cannula. This Example shows the utility of using a Nitinol cannula to inject cells and that the composition of the Nitinol and the diameter of the cannula are not detrimental to cell viability during delivery procedures described herein.

Example 3

Stem Cell Viability Based on Catheter Composition and Diameter

In order to further ascertain utility of various embodiments of the delivery device, mesenchymal stem cell viability was determined before and after injection through a Nitinol catheter.

A catheter constructed from Nitinol having a 0.011 inch diameter shows little adverse effect on cell viability as cells were injected/passed through the length of the catheter. Cell viability was similar to that of cells injected/passed through a stainless steel 18 g needle (0.049 inch diameter). However, unlike cells passed through the stainless steel needle, there was some cell loss in the catheter as compared to the 18 g needle.

In particular, cultured mesenchymal stem cells were harvested and viability verified by testing a sample via a trypan blue exclusion test. Cells were then broken into two groups for injection through either the 18 g stainless steel needle or the Nitinol catheter. After injection, cell viability was re-determined based on how many viable cells were present after exit from either the needle or the catheter. There were $5 \times 10^5$ viable cells after injection through the 18 g needle and $2.5 \times 10^5$ viable cells after injection through the Nitinol catheter. The number of dead cells passed through the 18 g needle and catheter were few in number.

This Example illustrates the capability of a Nitinol catheter to support cell viability in a manner similar to an 18 g stainless steel needle. However, unlike the data in Example 2, there was some cell loss by injection through the catheter (likely due to cell adherence to catheter walls). This Example shows the utility of using a Nitinol catheter to inject cells and that the composition of the Nitinol and the small diameter of the catheter are not detrimental to cell viability during delivery procedures described herein. The small diameter (and Nitinol composition) of the catheter provides unexpected utility for using a delivery device to deliver cells into sites where entry damage of the catheter should be minimized.

Example 4

Nitinol Based Catheter Provides Alternative to PEEK Based Catheters

Conventional catheter technology, where manipulation of the catheter is required, has utilized PEEK materials as the substance of choice. The present Example was performed to determine if Nitinol allowed for similar results in cell viability and number as standard PEEK composed catheters.

Mesenchymal stem cells were prepared as in Examples 2 and 3 and passed through an 18 g stainless steel needle, a 0.01 inch diameter PEEK catheter, a 0.007 inch diameter PEEK catheter and a 0.015 inch diameter Nitinol catheter.

The 0.015 inch diameter Nitinol catheter performs in a similar manner as the 0.01 and 0.007 inch PEEK catheters for delivery of viable cells.

Results for Example 4 illustrate the utility of using a Nitinol based catheter over of a PEEK based catheter. Because a Nitinol catheter has significant functional improvement in regard to shape memory and super elasticity over a PEEK catheter, the present results provide further support for use of Nitinol for catheter preparation.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A minimally invasive device for delivering a therapeutic to a target location in relation to a target site, the device comprising:
   an elongated hollow needle having a first end, a hollow shaft, and a second end, the first and the second ends forming openings and in communication along the hollow shaft of the elongated needle and the second end further defining a tip configured to allow insertion of the needle tip to the target site, wherein the hollow shaft of the needle is sufficiently rigid to maintain a pre-insertion shape during insertion of the needle tip to the target site;
   a cannula that sits internally within the hollow shaft of the needle, the cannula configured to advance along the shaft of the needle and through the opening at the tip of the needle, wherein a distal end of the cannula exits the tip of the needle in a preconfigured single constant-radius arch to full extension; and
   a catheter that sits internally within the cannula and is independently advanced in relation to the needle and cannula, the catheter capable of advancement though the preconfigured single constant-radius arch at the distal end of the cannula and into the target location of the target site;
   wherein the device, once positioned in the target location, is capable of delivering the therapeutic through the catheter to the target location in relation to the target site.

2. The device of claim 1 further comprising:
   an elongated handle assembly operably attached to the first end of the needle, the handle defining a passageway in communication with the opening in the first end of the needle, the passageway extending the length of the handle; and
   separate means within the passageway for accepting, attaching and independently advancing the cannula and catheter;
   wherein the handle has a port for receiving and allowing passage of the therapeutic into the catheter.

3. The device of claim 2 wherein the catheter is a spinal catheter.

4. The device of claim 2 wherein the handle port is a luer lock and the therapeutic is delivered to the handle by locking a syringe having the therapeutic to the luer lock on the handle.

5. The device of claim 2 wherein the therapeutic is stem cells.

6. The device of claim 5 wherein the stem cells are mesenchymal stem cells (MSCs).

7. The device of claim 1 wherein the cannula is made from a shape memory material.

8. The device of claim 7, wherein the shape memory material is a shape memory metal or a shape memory polymer.

9. The device of claim 7, wherein the shape memory material is Nitinol.

10. The device of claim 1 wherein the cannula and the catheter are made from a shape memory material.

11. The device of claim 1 wherein the target site is an intervertebral disc, a joint, a labrum or a ligament.

12. The device of claim 1 wherein the cannula forms a single constant-radius arch between 1° and 180° when fully advanced from the tip of the hollow needle, measured between the shaft of the hollow needle and the distal end of the cannula.

13. The device of claim 1, wherein the configuration of the single constant-radius arch is based on the target location.

14. The device of claim 1, wherein the cannula has a length of 0.1 to 4.0 inches.

15. The device of claim 1 wherein, upon insertion of the needle and the extension of the cannula and catheter to the target location, the distal end of the catheter is positioned at a distance from the first end of the elongated hollow needle that is less than the distance between the first end of the elongated hollow needle and the opening at the tip of the needle.

16. The device of claim 1 wherein the cannula forms a single constant-radius arch of greater than 90° when fully advanced from the tip of the hollow needle, measured between the shaft of the hollow needle and the distal end of the cannula.

17. A minimally invasive device for delivering a therapeutic to a target location in relation to a target site, the device comprising:
   an elongated hollow needle having a first end, a hollow shaft, and a second end, the first and the second ends forming openings and in communication along the hollow shaft of the elongated needle and the second end further defining a tip configured to allow insertion of the needle tip to the target site, wherein the hollow shaft of the needle is sufficiently rigid to maintain a pre-insertion shape during insertion of the needle tip to the target site; and
   a cannula that sits internally within the shaft of the elongated hollow needle, a distal end of the cannula configured to advance along the length of the needle and through the opening at the tip of the needle in a preconfigured single constant-radius arch to full extension;
   wherein the device, once positioned at the target location, is capable of delivering a therapeutic through the cannula to the target location.

18. The device of claim 17 further comprising:
   an elongated handle assembly operably attached to the first end of the needle, the handle defining a passageway in communication with the opening in the first end of the needle, the passageway extending the length of the handle; and
   means within the handle assembly for accepting, attaching and advancing the cannula within the needle;
   wherein the handle assembly has a port for receiving and allowing passage of the therapeutic into the cannula.

19. The device of claim 18 wherein the handle port is a luer lock and the therapeutic are delivered to the handle by locking a syringe having the therapeutic to the luer lock on the handle.

20. The device of claim 17 wherein the therapeutic is stem cells.

21. The device of claim 20 wherein the stem cells are mesenchymal stem cells (MSCs).

22. The device of claim 17 wherein the cannula is made from a shape memory material.

23. The device of claim 22, wherein the shape memory material is a shape memory metal or a shape memory polymer.

24. The device of claim 22, wherein the shape memory material is Nitinol.

25. The device of claim 17 wherein the target site is an invertebral disc, a joint, a labrum or a ligament.

26. The device of claim 17 wherein the cannula forms a single constant-radius arch of between 1° and 180° when fully advanced out the tip of the hollow needle, measured between the shaft of the hollow needle and the distal end of the cannula.

27. The device of claim 17, wherein the configuration of the single constant-radius arch is based on the target location.

28. The device of claim 17, wherein the cannula has a length of 0.1 to 4.0 inches.

29. The device of claim 17 wherein, upon insertion of the needle and the extension of the cannula to the target location, the distal end of the cannula is positioned at a distance from the first end of the elongated hollow needle that is lesser than the distance between the first end of the elongated hollow needle and the opening at the tip of the needle.

30. The device of claim 17 wherein the cannula forms a single constant-radius arch of greater than 90° when fully advanced from the tip of the hollow needle, measured between the shaft of the hollow needle and the distal end of the cannula.

31. A minimally invasive device for delivering a therapeutic to a target location in relation to a target site, the device comprising:

a needle assembly having an elongated needle with a first end and a second end, the first and the second ends forming openings in communication along the length of the elongated needle and the second end further defining a tip configured to allow insertion of the needle assembly to the target site, wherein the elongated needle is sufficiently rigid to maintain a pre-insertion shape during insertion of the needle tip to the target site, and wherein the needle assembly further comprises a cannula that sits internally within the elongated needle, the cannula configured to advance along the length of the needle and through the opening at the tip of the needle in a preconfigured single constant-radius arch to full extension;

an adapter that operably attaches to the needle assembly, the adapter configured with a port for connection to the therapeutic, the adapter configured to reduce shearing force on the therapeutic once the therapeutic enters the adapter;

wherein the device, once positioned at the target site, is capable of delivering the therapeutic through the cannula of the needle assembly to the target location within the target site.

32. The device of claim 31 further comprising a handle assembly, the handle assembly defining a passageway in communication with the adapter and needle assembly, the passageway extending the length of the handle.

33. The device of claim 31 wherein, upon insertion of the needle and the extension of the cannula to the target location, the distal end of the cannula is positioned at a distance from the first end of the elongated hollow needle that is lesser than the distance between the first end of the elongated hollow needle and the opening at the tip of the needle.

34. The device of claim 31 wherein the cannula forms a single constant-radius arch of greater than 90° when fully advanced from the tip of the hollow needle, measured between the shaft of the hollow needle and the distal end of the cannula.

* * * * *